(12) United States Patent
Hong et al.

(10) Patent No.: US 11,826,029 B2
(45) Date of Patent: *Nov. 28, 2023

(54) SELF-CLOSING DEVICES AND METHODS FOR MAKING AND USING THEM

(71) Applicant: Solinas Medical Inc., Santa Clara, CA (US)

(72) Inventors: James Hong, Sunnyvale, CA (US); Michael J. Drews, Palo Alto, CA (US)

(73) Assignee: Solinas Medical Inc., Santa Clara, CA (US)

(*) Notice: Subject to any disclaimer, the term of this patent is extended or adjusted under 35 U.S.C. 154(b) by 323 days.

This patent is subject to a terminal disclaimer.

(21) Appl. No.: 16/915,890

(22) Filed: Jun. 29, 2020

(65) Prior Publication Data
US 2020/0397420 A1   Dec. 24, 2020

Related U.S. Application Data

(60) Continuation of application No. 15/853,784, filed on Dec. 23, 2017, now Pat. No. 10,695,040, which is a
(Continued)

(51) Int. Cl.
*A61F 2/07* (2013.01)
*A61B 17/11* (2006.01)
(Continued)

(52) U.S. Cl.
CPC .......... *A61B 17/0057* (2013.01); *A61B 17/11* (2013.01); *A61B 17/3403* (2013.01);
(Continued)

(58) Field of Classification Search
CPC ............... A61B 17/0057; A61B 17/11; A61B 2017/1107; A61B 2017/00867; A61B 2017/1132; A61F 2/064; A61F 2002/065; A61F 2002/061; A61F 2/92; A61F 2/962; A61F 2/07; A61F 2/06; A61F 2/82;
(Continued)

(56) References Cited

U.S. PATENT DOCUMENTS 3,726,279 A * 4/1973 Barefoot ................ A61B 17/11
606/151
5,007,926 A * 4/1991 Derbyshire ............... A61F 2/92
606/191
(Continued)

*Primary Examiner* — Seema Mathew
(74) *Attorney, Agent, or Firm* — VISTA IP LAW GROUP LLP; William A English

(57) ABSTRACT

A self-closing device for implantation within a patient's body includes base material including an inner surface area for securing the base material to a tissue structure, and a plurality of support elements surrounding or embedded in the base material. The support elements are separable laterally within a plane of the base material to accommodate creating an opening through the base material for receiving one or more instruments through the base material, and biased to return laterally towards a relaxed state for self-closing the opening after removing the one or more instruments. The device may be provided as a patch or integrally attached to a tubular graft or in various shapes.

27 Claims, 16 Drawing Sheets

Related U.S. Application Data continuation of application No. 14/813,044, filed on Jul. 29, 2015, now Pat. No. 9,848,860, which is a division of application No. 13/607,783, filed on Sep. 9, 2012, now Pat. No. 9,427,218, which is a continuation-in-part of application No. PCT/US2011/027796, filed on Mar. 9, 2011.

(60) Provisional application No. 61/385,483, filed on Sep. 22, 2010, provisional application No. 61/312,183, filed on Mar. 9, 2010.

(51) Int. Cl.
| | |
|---|---|
| *A61B 17/00* | (2006.01) |
| *A61M 39/02* | (2006.01) |
| *A61B 17/34* | (2006.01) |
| *A61M 1/36* | (2006.01) |
| *A61B 90/00* | (2016.01) |
| *A61B 17/12* | (2006.01) |
| *A61F 2/06* | (2013.01) |

(52) U.S. Cl.
CPC ........... *A61B 90/39* (2016.02); *A61M 1/3655* (2013.01); *A61M 39/0247* (2013.01); *A61B 2017/00592* (2013.01); *A61B 2017/00597* (2013.01); *A61B 2017/00676* (2013.01); *A61B 2017/00862* (2013.01); *A61B 2017/00867* (2013.01); *A61B 2017/00876* (2013.01); *A61B 2017/1107* (2013.01); *A61B 2017/1135* (2013.01); *A61B 2017/12004* (2013.01); *A61B 2090/3962* (2016.02); *A61B 2090/3966* (2016.02); *A61F 2/064* (2013.01); *A61F 2210/009* (2013.01); *A61M 2039/0258* (2013.01); *A61M 2039/0261* (2013.01); *A61M 2039/0291* (2013.01)

(58) Field of Classification Search
CPC .... A61F 2/856; A61F 2/90; A61F 2220/0075; A61F 2220/0008; A61F 2/97; A61F 2002/072; A61F 2002/821; A61F 2210/0076; A61F 2/04; A61F 2002/823; A61M 1/3655; A61M 2039/0258; A61M 39/0247; A61M 2039/0261; A61M 1/3653; A61M 39/02; A61M 27/002; A61M 39/0208; A61M 39/06; A61M 1/3661

See application file for complete search history.

(56) References Cited

U.S. PATENT DOCUMENTS

| | | | | |
|---|---|---|---|---|
| 5,383,926 A | * | 1/1995 | Lock | A61F 2/92 606/198 |
| 5,643,340 A | * | 7/1997 | Nunokawa | A61F 2/064 623/1.49 |
| 5,653,743 A | * | 8/1997 | Martin | A61F 2/07 623/1.35 |
| 6,261,257 B1 | * | 7/2001 | Uflacker | A61M 1/3655 604/9 |
| 6,685,726 B2 | * | 2/2004 | Black | A61B 17/00491 606/213 |
| 6,726,923 B2 | * | 4/2004 | Iyer | A61P 41/00 424/443 |
| 7,381,222 B2 | * | 6/2008 | Pflueger | A61F 2/203 623/14.11 |
| 8,945,203 B2 | * | 2/2015 | Shalev | A61F 2/90 623/1.13 |
| 9,486,344 B2 | * | 11/2016 | Xue | A61F 2/07 |
| 10,004,507 B2 | * | 6/2018 | Asfora | A61B 17/06166 |
| 10,219,808 B2 | * | 3/2019 | Tihon | A61B 17/1325 |
| 10,299,794 B2 | * | 5/2019 | Orion | A61M 1/3655 |
| 10,434,293 B2 | * | 10/2019 | Park | A61M 27/002 |
| 10,925,710 B2 | * | 2/2021 | Hall | A61F 2/06 |
| 2004/0010303 A1 | * | 1/2004 | Bolea | A61N 1/36053 607/116 |
| 2004/0010308 A1 | * | 1/2004 | Zafrir-Pachter | A61F 2/82 623/1.22 |
| 2005/0137614 A1 | * | 6/2005 | Porter | A61M 1/3655 606/153 |
| 2006/0052866 A1 | * | 3/2006 | Gilles | A61B 17/12013 623/1.51 |
| 2006/0069426 A1 | * | 3/2006 | Weinberger | A61F 2/06 623/1.18 |
| 2006/0100648 A1 | * | 5/2006 | Roy | A61B 17/0644 606/153 |
| 2006/0281966 A1 | * | 12/2006 | Peacock, III | A61F 2/92 623/1.13 |
| 2007/0233229 A1 | * | 10/2007 | Berra | A61F 2/856 623/1.13 |
| 2008/0167725 A1 | * | 7/2008 | Pflueger | A61F 5/566 623/23.7 |
| 2008/0195060 A1 | * | 8/2008 | Roger | A61M 1/3661 604/246 |
| 2010/0070019 A1 | * | 3/2010 | Shalev | A61F 2/06 623/1.46 |
| 2010/0121247 A1 | * | 5/2010 | Yang | A61M 1/3655 623/1.1 |
| 2010/0130995 A1 | * | 5/2010 | Yevzlin | A61B 17/11 606/153 |
| 2010/0292774 A1 | * | 11/2010 | Shalev | A61F 2/06 623/1.13 |
| 2012/0058249 A1 | * | 3/2012 | House | B29D 23/001 427/2.25 |
| 2013/0041453 A1 | * | 2/2013 | Consigny | A61M 1/3655 623/1.42 |
| 2015/0051532 A1 | * | 2/2015 | Tomko | A61M 1/3661 604/8 |
| 2016/0199085 A1 | * | 7/2016 | Hong | A61B 17/32 604/500 |
| 2017/0014612 A1 | * | 1/2017 | Lundgren | A61M 5/14 |

\* cited by examiner

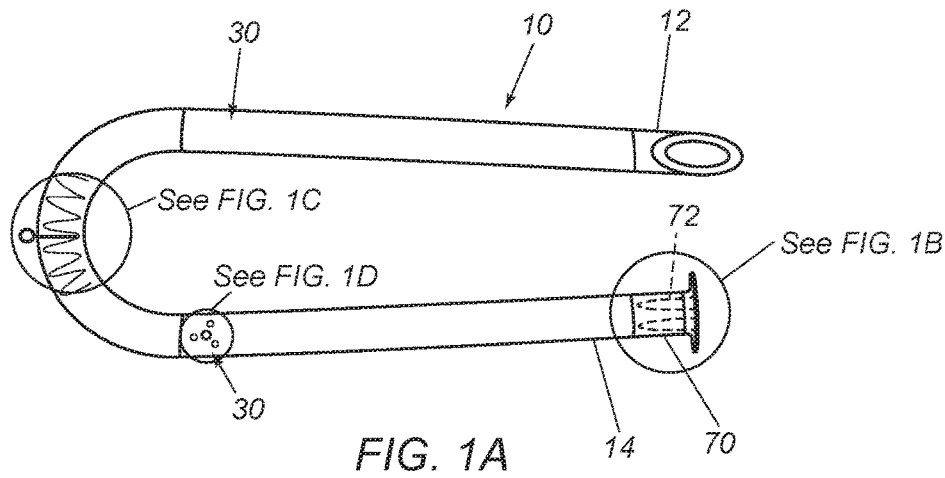
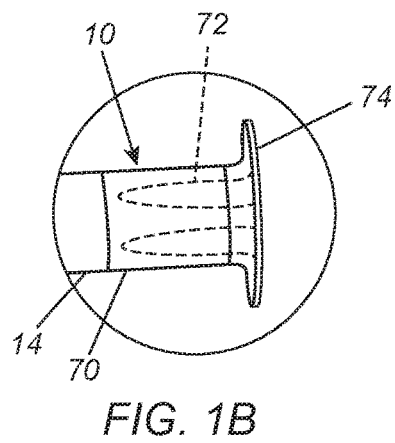
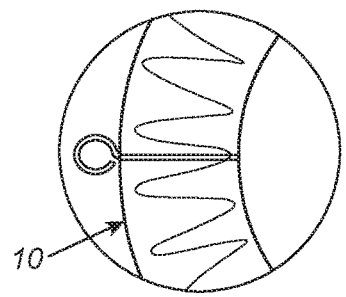
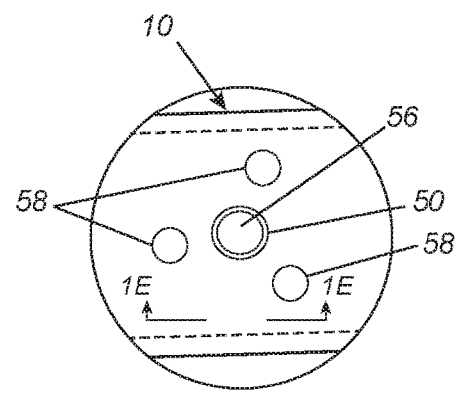
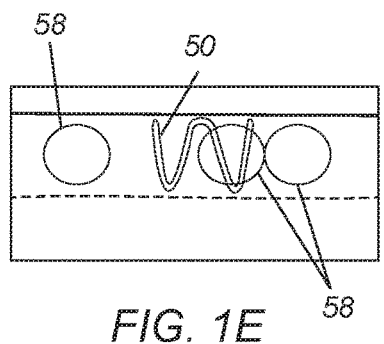

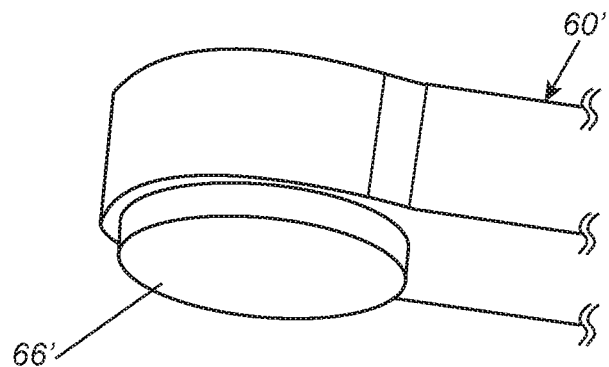
FIG. 6
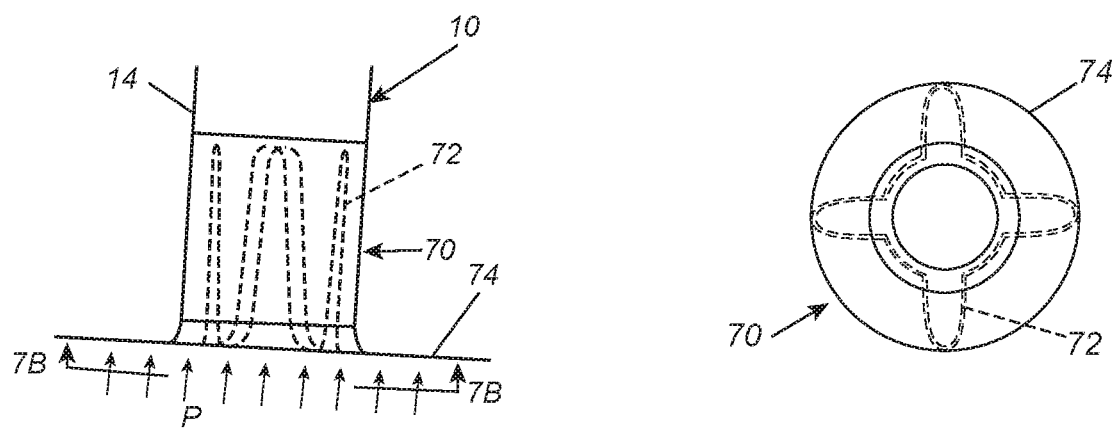
FIG. 7A
FIG. 7B
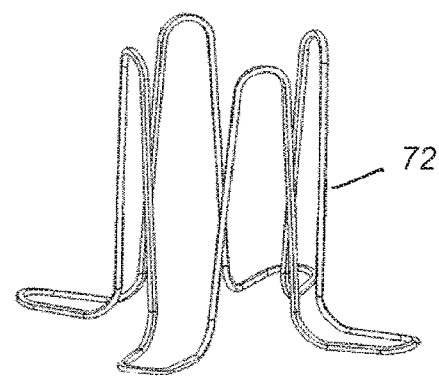
FIG. 7C

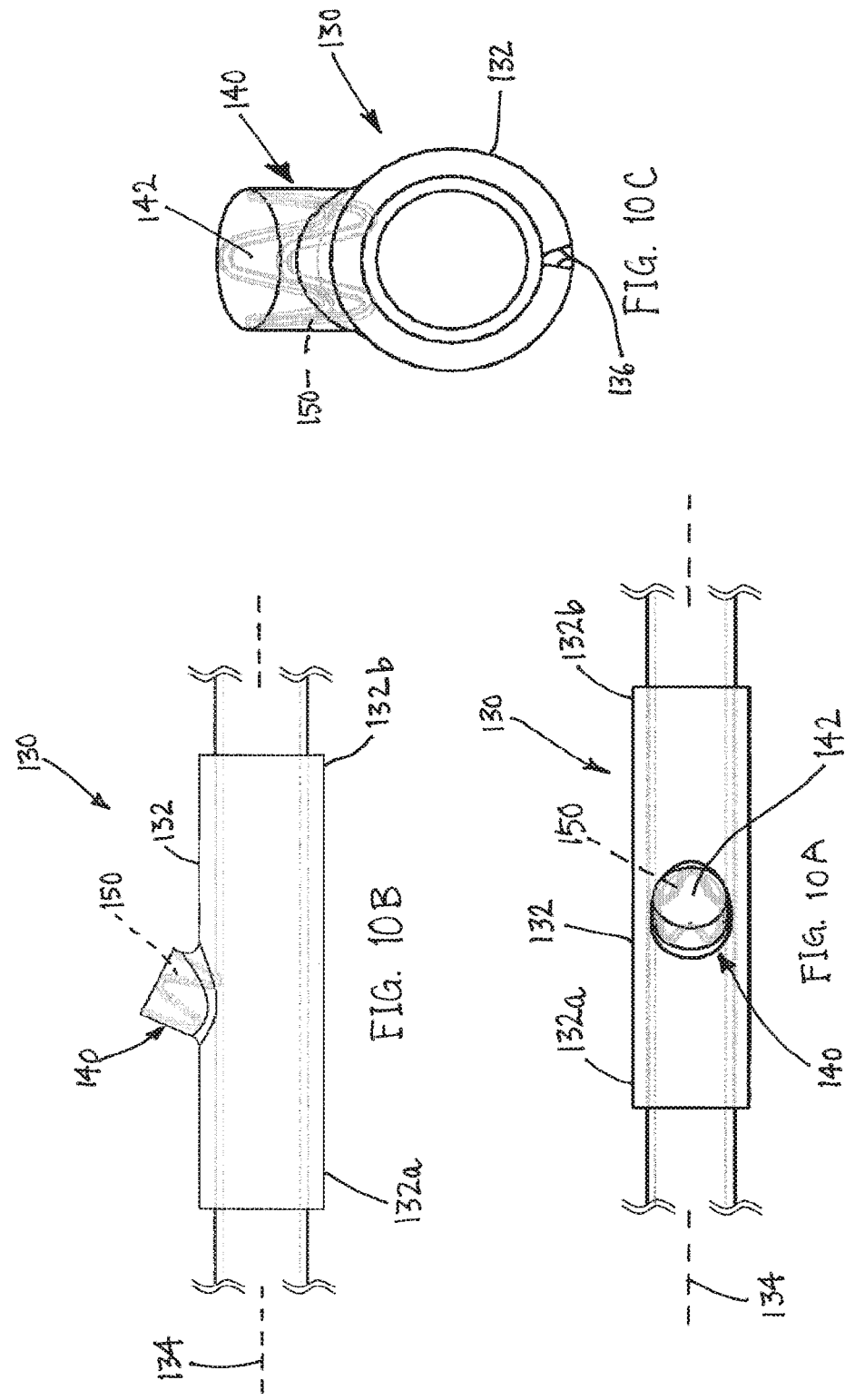

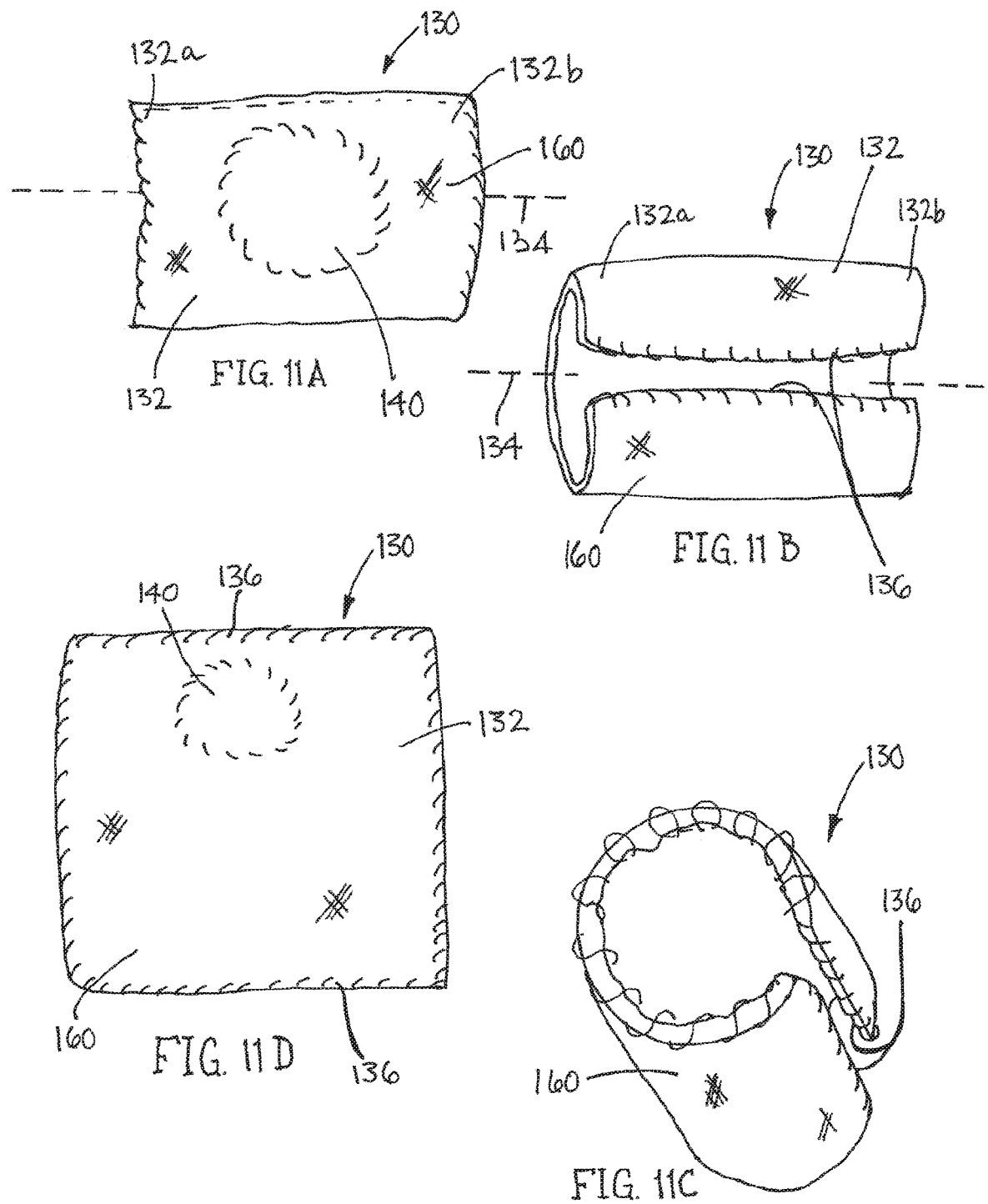

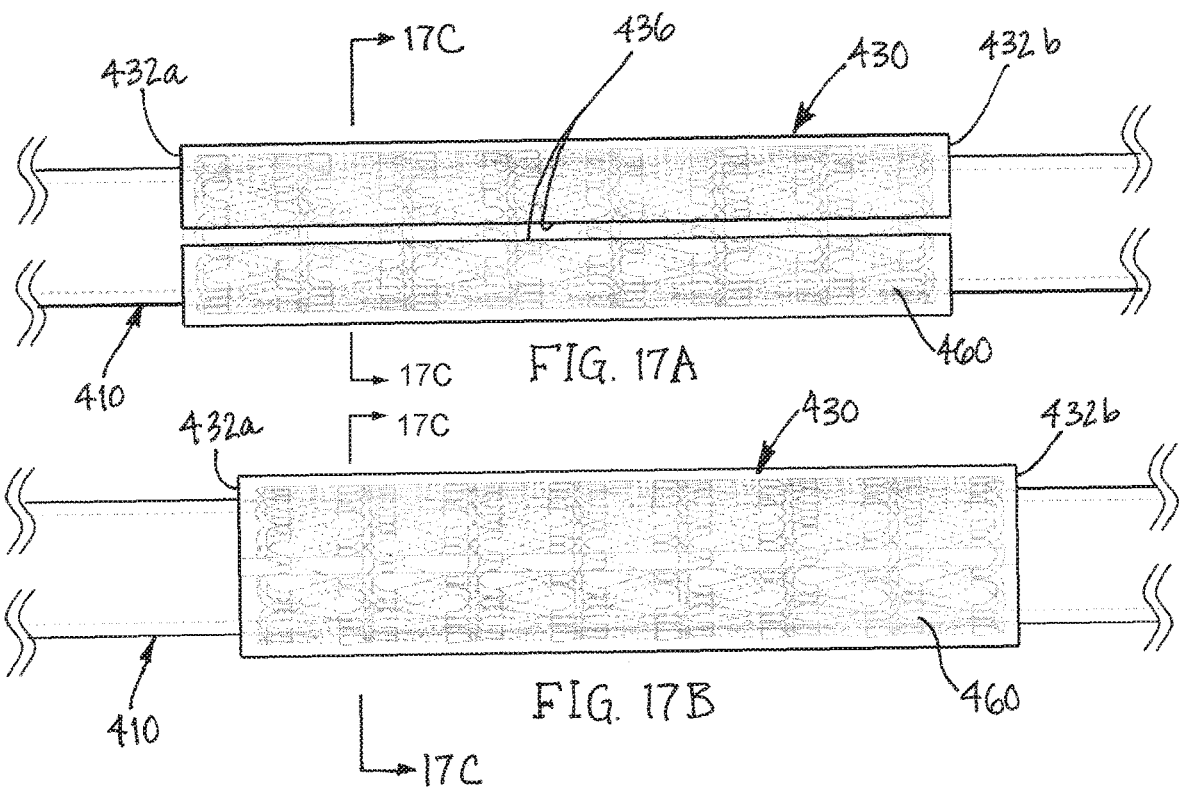
FIG. 17A
FIG. 17B
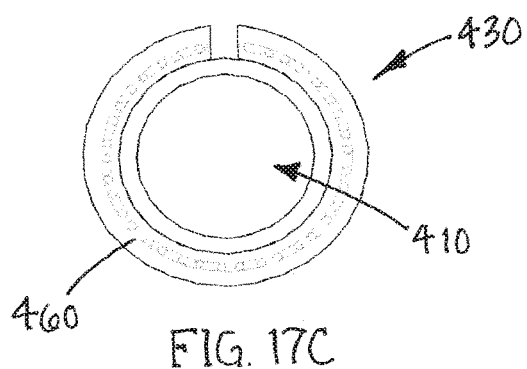
FIG. 17C
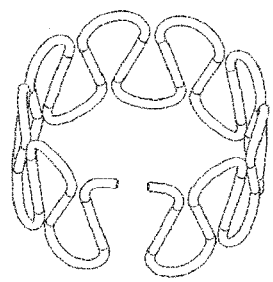
FIG. 17D

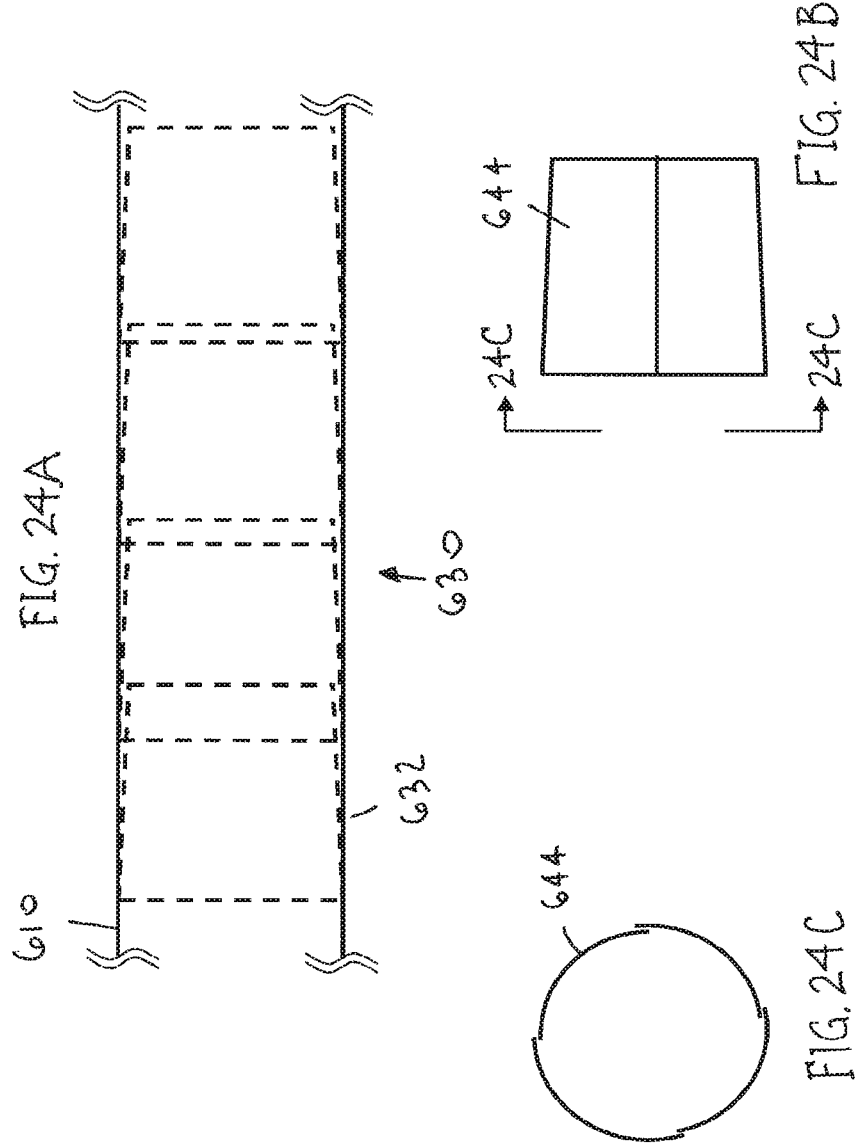

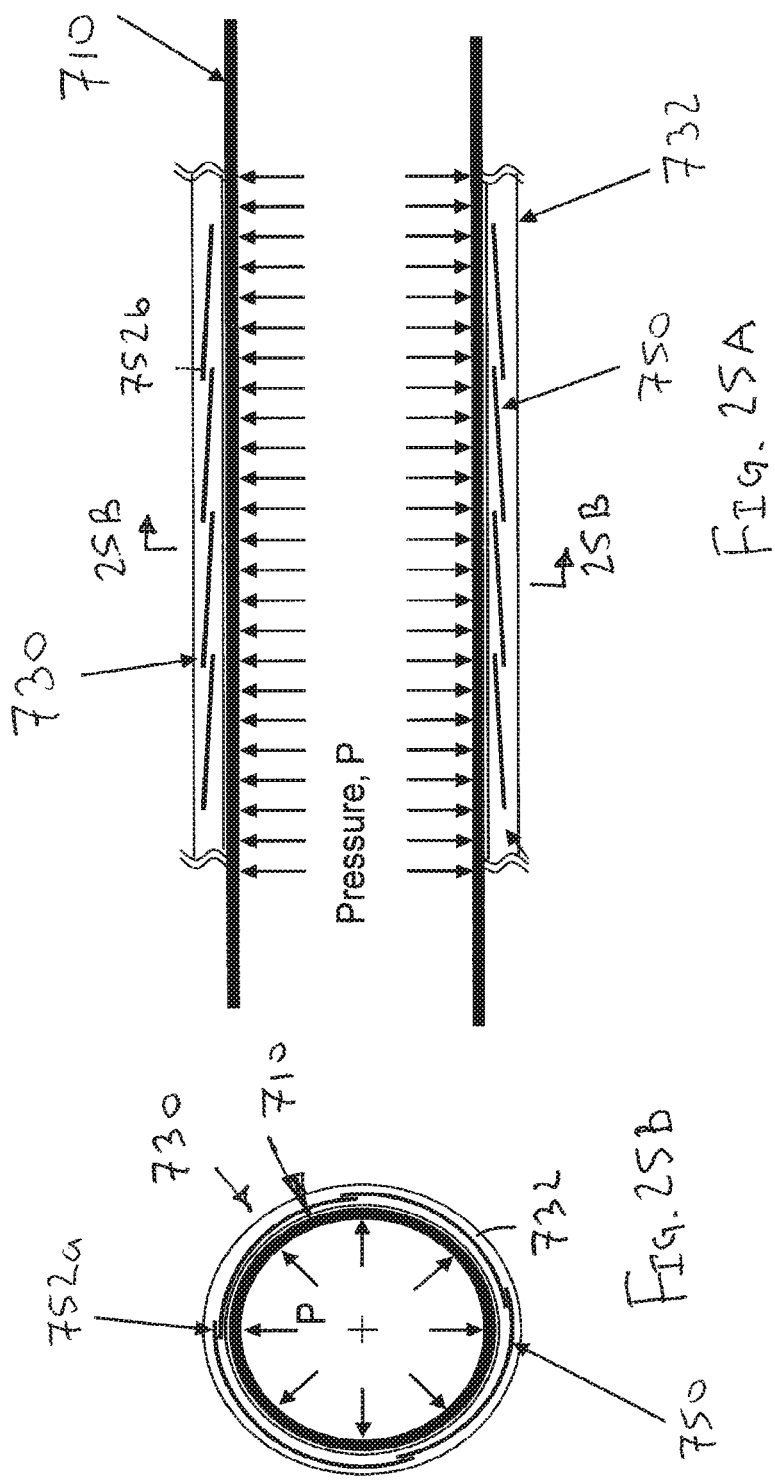

SELF-CLOSING DEVICES AND METHODS FOR MAKING AND USING THEM

RELATED APPLICATION DATA

This application is a continuation of co-pending application Ser. No. 15/853,784, filed Dec. 23, 2017, and issuing as U.S. Pat. No. 10,695,040, which is a continuation of application Ser. No. 14/813,044, filed Jul. 29, 2015, now U.S. Pat. No. 9,848,860, which is a divisional of application Ser. No. 13/607,783, filed Sep. 9, 2012, now U.S. Pat. No. 9,427,218, which is a continuation-in-part of International Application No. PCT/US2011/027796, filed Mar. 9, 2011, which claims benefit of provisional application Ser. No. 61/312,183, filed Mar. 9, 2010, and 61/385,483, filed Sep. 22, 2010, the entire disclosures of which are expressly incorporated by reference herein.

FIELD OF THE INVENTION

The field of the invention generally relates to self-closing devices that are implantable within a patient's body and to apparatus, systems, and methods including such self-closing devices. For example, the present invention may include self-closing tubular structures, cuffs, or patches, and/or grafts that include resealable access ports or regions including self-closing tubular structures, and/or may include systems and methods for implanting such self-closing structures and/or grafts.

BACKGROUND

Dialysis for end stage renal disease ("ESRD") is one of the leading and rapidly growing problems facing the world today. In 2006, there were greater than fifty one million (51,000,000) people in the United States diagnosed with chronic kidney disease. Greater than five hundred thousand (500,000) people in this population suffered from ESRD. With the growing aging population and increasing prevalence of high risk factors such as diabetes (35% of all ESRD patients, Szycher M., *J Biomater Appl.* 1999; 13, 297-350) and hypertension (30%), the projected population in 2020 is greater than 784,000 (est. USRDS 2008).

The two primary modes of treatment are kidney transplant and hemodialysis. Due to the shortage of available transplant kidneys, approximately seventy percent (70%) of people with ESRD undergo hemodialysis (USRDS 2008) for life or until a transplant kidney becomes available. To facilitate the frequent, periodic treatments, patients must undergo vascular surgery to prepare their artery and vein, typically in their forearm, for dialysis. The two most common methods of preparing the artery and vein are arteriovenous (AV) fistulas and AV grafts—the former is the preferred option due to longer patency rates; however fistulas are often replaced by AV grafts once the life of the fistula has been exhausted.

There are advantages and disadvantages to both methods. Most notably, grafts are easy to implant, and ready to use relatively sooner, but have shorter lifespans and are more prone to infection and thrombus formation. Fistulas have greater durability and are less prone to infection, but can take up to six (6) months (KDOQI) to mature before use, and the veins used for access have tendencies to develop pseudoaneurysms at the site of repeated access. One of the contributing factors to the rapid degradation of current AV grafts and/or veins is the repeated needle sticks during dialysis with relatively large needles (e.g., 14-16 Gauge). This is exacerbated because the average patient undergoes hemodialysis treatment two or three times a week, every week of every year until a kidney replacement is available or until the end of their life expectancy, which is approximately ten (10) years (Szycher M., *J Biomater Appl.* 1999; 13, 297-350). Moreover, due to the high risk of intimal hyperplasia and vessel narrowing, dialysis patients also undergo periodic interventional treatment to maintain patent vessels, which may occur several times a year. This typically involves angioplasty or stenting, akin to the treatment of coronary vascular occlusions, and vascular access using needles is also needed for these procedures, thereby contributing to the risk of graft or vessel degradation.

Therefore, there is an apparent need for devices, systems, and methods for treating ESRD and other conditions.

SUMMARY

The present application generally relates to self-closing devices that are implantable within a patient's body and to apparatus, systems, and methods including such self-closing devices. For example, apparatus, systems, and methods described herein may include self-closing tubular structures, cuffs, or patches, and/or grafts that include resealable access ports or regions including self-closing structures.

In accordance with an exemplary embodiment, a Circular Elastic Band ("CEB") may be provided that is made of a biocompatible material with design features suitable for multiple clinical applications. In general, the CEB may be expanded radially outwardly and, when released, may elastically return radially inwardly towards its original shape while compressing material contained within its inner diameter. The CEB may be used, for example, in one or more of the following applications to close an opening in the wall(s) of a tubular structure or tissue wall while facilitating repeated re-access and re-closure, or restrict (or prevent) and control material flow through a tubular structure: facilitating repeated re-access in an arteriovenous (AV) vascular grafts for hemodialysis; closing a vascular opening in a vessel wall after an endovascular procedure; or closing patent foramen ovale (PFO closure).

For example, in applications where a pressure gradient may exist across the CEB, the strength of the closure may be sufficient to prevent leakage.

In accordance with another embodiment, a self-sealing access device is provided that includes base material, e.g., elastomeric and/or bioabsorbable material, including a surface area for securing the base material to a tissue structure; and a plurality of support elements surrounding or embedded in the base material. The support elements may be separable to accommodate creating an opening through the base material for receiving one or more instruments through the base material, and biased to return towards a relaxed state for self-closing the opening after removing the one or more instruments. In exemplary embodiments, the device may be a cuff, a patch, or other device that may be secured around or to a tubular, curved, or substantially flat body structure.

For example, the support elements may include a plurality of struts spaced apart from one another to define openings in a relaxed or relatively low stress state. The struts may be separable from one another, e.g., to a relatively high stress state, to accommodate receiving one or more instruments through the openings and the base material filling or adjacent to the openings, the struts resiliently biased to return towards one another, e.g., to the relaxed or relatively low stress state.

In accordance with still another embodiment, a method is provided for implanting an access port into a patient's body that includes exposing a tubular body or other surface within a patient's body, e.g., a curved or substantially flat surface of a tubular body or other tissue structure, such as a vessel or graft, a heart, or a wall of the abdomen; and attaching an access port to the outer surface of the tubular body or tissue structure. The access port may include base material and a plurality of support elements, the support elements separable to accommodate creating an opening through the base material for receiving one or more instruments through the base material, and biased to return towards a relaxed or relatively low stress state for self-closing the opening after removing the one or more instruments.

In accordance with yet another embodiment, a system or kit is provided for accessing a tissue structure or graft implanted within a patient's body that includes a self-closing access device and an instrument for providing access through the access device. For example, the access device may include a cuff or patch that may be attached to the tissue structure or graft, e.g., including base material, e.g., elastomeric and/or bioabsorbable material, and a plurality of support elements surrounding or embedded in the base material.

In an exemplary embodiment, the instrument may be a needle including a tip insertable through the base material between one or more of the support elements. The tip of the needle may be configured to facilitate passing the needle between the support elements, e.g., including at least one of a coating, a surface treatment, and the like, to facilitate passing the needle between the support elements. In addition, the tip may be beveled or tapered, e.g., including a beveled shape, to facilitate inserting the needle through the base material between the support elements. Optionally, the support elements may be configured to facilitate inserting the needle therethrough, e.g., including tapered or rounded edges.

In addition or alternatively, the instrument may include one or more features for limiting the depth of penetration of the tip through the access device. For example, the needle may include a bumper spaced apart a predetermined distance from the tip to prevent over-penetration of the needle through the access device.

In accordance with still another embodiment, an implantable graft is provided that includes an elongate tubular graft including first and second ends and a graft lumen extending therebetween; and an anastomotic flow coupler on the first end for coupling the graft to a body lumen. Optionally, the graft may also include an access port in a sidewall of the tubular member, e.g., similar to any of the embodiments herein. In one example, the first end is attached to a vein and the second end is attached to an artery.

In one embodiment, the coupler may include a flexible tubular body extending from the first end and an elastic support structure supporting the tubular body. The support structure may support the tubular body, e.g., to reduce kinking or buckling, or may be biased to expand the tubular body to a first diameter, yet may be resiliently compressible to allow insertion into a body lumen. For example, at least a portion of the support structure may be biased to expand the tubular body to a diameter larger than an inner diameter of the body lumen to enhance remodeling of the body lumen once the coupler is secured therein.

In another embodiment, the coupler may include a self-expanding frame attached to the first end of the tubular graft and a flared rim extending from the frame for securing the first end relative to a body lumen. In yet another embodiment, the coupler may include a balloon expandable frame attached to the first end of the tubular graft, the frame being plastically deformable to form a flared rim extending from the graft for securing the first end relative to a body lumen. In still another embodiment, the coupler may include a tubular mesh coupled to the first end of the tubular graft at an intermediate location on the tubular mesh between open ends such that the graft lumen communicates with an interior of the tubular mesh. In another embodiment, the coupler may include a self-expanding frame attached to the first end of the tubular graft and a tubular mesh coupled to the frame at an intermediate location on the tubular mesh.

In accordance with yet another embodiment, an access port is provided for a tubular structure within a patient's body that includes a port body including a first end, a second end, and a wall extending between the first and second ends defining side edges extending between the first and second ends, e.g., substantially parallel to a longitudinal axis, and a plurality of bands embedded in or surrounding the port body. Each band may include a plurality of struts including spaces therebetween, the struts being separable to create a passage through the port body to accommodate an instrument being introduced therethrough the port body and resiliently biased to compress the port body to close the passage.

In one embodiment, the port body may be a patch, optionally, including a sewing ring around its periphery. Alternatively, the port body may be a cuff or an enclosed tubular body.

In accordance with still another embodiment, a method is provided for accessing a body structure within a patient's body that includes providing an access port comprising a port body including a first end, a second end, and a wall extending between the first and second ends defining side edges extending between the first and second ends, e.g., substantially parallel to a longitudinal axis, and a plurality of bands embedded in or surrounding the port body, each band comprising a plurality of struts defining a zigzag pattern; the method further including attaching the port body to a body structure. In exemplary embodiments, the port body may be a tubular body, a "C" shaped body or other cuff, or a patch, e.g., having a curved, flat, conical, or other shape. Thereafter, one or more instruments may be inserted through the port body into the body structure, the struts of the bands separating to create a passage through the port body. The bands may be resiliently biased to compress the port body or otherwise return towards their original configuration to close the passage after the one or more instruments are removed from the port body.

In accordance with yet another embodiment, an access port is provided for a tubular structure within a patient's body that includes a port body including a first end, a second end, and a wall extending between the first and second ends defining side edges extending between the first and second ends, e.g., substantially parallel to a longitudinal axis; and a side port extending transversely from the port body. A band may be embedded in or surrounding the side port, the band including a plurality of struts defining a zigzag pattern. The band may be expandable from a contracted condition to an enlarged condition to accommodate receiving one or more instruments through the side port, yet biased to return towards the contracted condition to compress the side port radially inwardly to seal the side port after the one or more instruments are removed therefrom.

In accordance with another embodiment, an arteriovenous graft system is provided that includes an elongate tubular graft including first and second ends and a graft lumen extending therebetween; an access port in a sidewall of the tubular member; and a locator device. In an exemplary embodiment, the access port may include a tubular member including first and second ends and defining an access lumen extending between the first and second ends. The tubular member may be expandable from a contracted condition to an enlarged condition to allow access to the graft lumen, yet biased to return towards the contracted condition to substantially seal the access lumen.

In addition, the access port may include one or more locator elements, e.g., a first plurality of ferromagnetic elements disposed around the tubular member. The locator device may include a proximal end, and a distal end including a second plurality of ferromagnetic elements disposed around a passage. The second plurality ferromagnetic elements may be disposed around the passage in a configuration similar to the first plurality of ferromagnetic elements such that the distal end of the locator device is magnetically attracted to the access port such that the passage is aligned with the access lumen of the tubular member to facilitate introducing one or more instructions through the passage and access lumen into the graft lumen.

In another embodiment, the locator device may include a proximal end, a distal end including a passage therethrough for receiving one or more instruments therethrough, and an inductance meter on the distal end adjacent the passage for detecting when the passage is aligned with the access lumen of the tubular member, e.g., to facilitate introducing one or more instructions through the passage and access lumen into the graft lumen.

Other aspects and features of the present invention will become apparent from consideration of the following description taken in conjunction with the accompanying drawings and Appendices.

BRIEF DESCRIPTION OF THE DRAWINGS

The drawings illustrate exemplary embodiments, in which:

FIG. 1A is a top view of an exemplary embodiment of an arteriovenous graft including self-closing access ports.

FIG. 1B is a detail of one end of the graft of FIG. 1A, showing an anastomotic connector thereon.

FIG. 1C is a detail of the graft of FIG. 1 showing an embedded helical spine in the graft wall.

FIGS. 1D and 1E are top and side views, respectively, of an access port in the graft of FIG. 1A.

FIG. 6 is a detail of a distal end of an alternative embodiment of an instrument for locating an access port, similar to that shown in FIGS. 5A and 5B, including an antiseptic pad.

FIGS. 7A and 7B are side and end views, respectively, of a sutureless anastomosis connector that may be provided on a tubular graft, such as that shown in FIG. 1A.

FIG. 7C is a perspective view of an elastic frame that may be provided on the connector of FIGS. 7A and 7B.

FIGS. 10A-10C are side, top, and end views, respectively, of an embodiment of an access port, including a circular elastic band ("CEB") embedded in a silicone sleeve (with fabric covering not shown), and attached to a tubular graft.

FIGS. 11A-11C are top, bottom, and end views, respectively, of the sleeve of FIGS. 10A-10C split along a length of the sleeve and covered with fabric to provide a cuff with integral access port.

FIG. 11D is a bottom view of the cuff of FIGS. 11A-11C with the cuff opened and substantially flattened.

FIGS. 17A and 17B are bottom and top views, respectively, of the silicone sleeve and tubing of FIGS. 16A and 16B with the silicone sleeve covered with fabric to provide an integral access port.

FIG. 17C is a cross-sectional view of the access port and tubing of FIGS. 17A and 17B, taken along lines 17C-17C.

FIG. 17D is a perspective view of an exemplary embodiment of one of the bands that may be embedded in the silicone sleeve of FIGS. 16A-17C.

FIG. 24A is a top view of another embodiment of an access port including a plurality of overlapping bands in adjacent frustoconical shapes.

FIGS. 24B and 24C are side and end views of an individual frustoconical access port member that may be included in the access port of FIG. 24A.

FIG. 25A is a cross-section view of a tubular body structure including the access port of FIGS. 24A-24C implanted around the structure.

FIG. 25B is a cross-section of the tubular body structure and access port of FIG. 25A, taken along lines 25B-25B.

DETAILED DESCRIPTION OF THE EXEMPLARY EMBODIMENTS

Turning to the drawings, FIG. 1A shows an exemplary embodiment of an arteriovenous graft 10 that includes multiple self-closing access ports 30, e.g., each including a circular elastic band ("CEB") 50, e.g., as shown further in FIGS. 1D and 1E. The CEBs 50 may be preformed within the AV graft, e.g., to provide two ports for standard arterial and venous access, as shown. Optionally, a plurality of ferromagnetic elements 58 may be provided around or otherwise adjacent the CEB 50, e.g., to facilitate identifying and/or locating the access port 30, as described in the applications incorporated by reference herein. The graft 10 may be fabricated from well-known synthetic or biological material for vascular grafts, and the embedded port access (PA) sites may be used for access and re-access during hemodialysis using standard gauge needles, e.g., fourteen or sixteen gauge (14G-16G) needles, through the center region of the structure.

The access port 30 may also be used during standard angioplasty, vascular stenting, or thrombectomy procedures to manage and maintain AV patency for dialysis. The structure of the CEB 50 may elastically expand radially outwardly, and, upon removal of the dialysis needle, the structure may largely return to its original size and shape without any (or significant) permanent deformation and create an immediate seal by compressing the material within the structure.

The graft 10 may be surgically or percutaneously implanted using standard techniques of making standard incisions and/or forming suture based anastomotic junctions or unique methods of using sutureless based anastomotic junctions. As the AV graft 10 is implanted, the elastic structure may be strategically placed subcutaneously for easy access. Furthermore, optionally, the CEB subassembly (or any of the other access devices described herein) may be augmented with features or components that may facilitate identification of the access site(s) for the insertion of a dialysis needle or catheterization instruments, as described further below.

Figure 2:
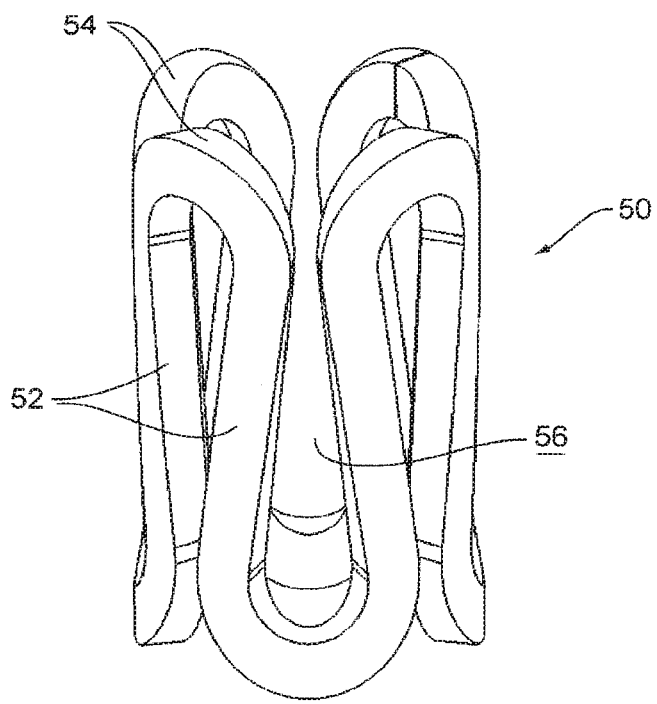
FIG. 2 is a perspective view of an exemplary embodiment of a self-closing device, namely a circular elastic band ("CEB"), that may be incorporated into an access port, such as that shown in FIGS. 1D and 1E.
Figure 3:
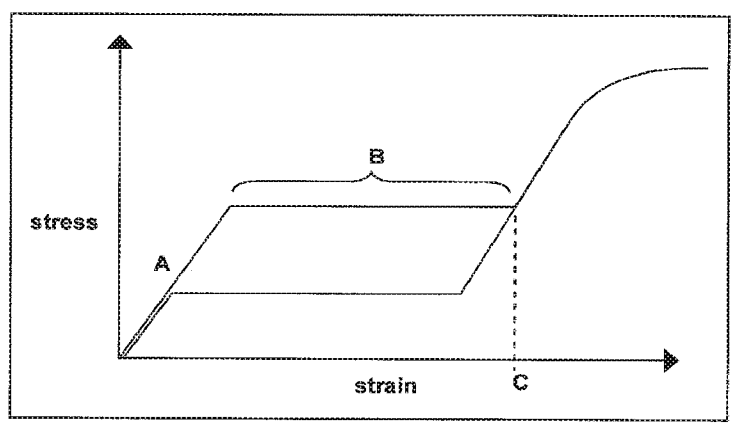
FIG. 3 is a graph showing an idealized stress-strain curve for Nitinol material.
Figure 4A:
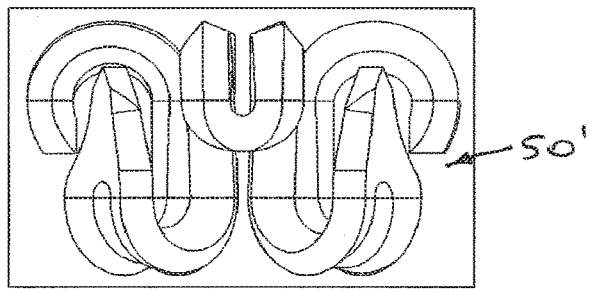
FIGS. 4A and 4B are side and perspective views, respectively, of another exemplary embodiment of a self-closing device, namely a conduit closure device ("CCD"), which, alternatively, may be incorporated into an access port.
Figure 4B:
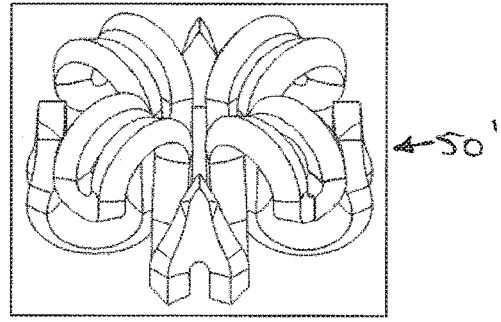

FIG. 2 shows an exemplary embodiment of a circular elastic band or "CEB" 50 that generally includes a tubular member sized for implantation in a patient's body, e.g., either alone or incorporated into another device or system. FIGS. 4A and 4B show an alternative embodiment of a CEB 50' that may be used instead of CEB 50. For example, the CEB 50 may be embedded or otherwise incorporated into the AV graft shown in FIGS. 1A 1D, and 1E. Alternatively, the CEB 50 may be implanted directly into tissue, e.g., to seal a puncture or other opening through tissue, as disclosed in the applications incorporated by reference herein.

The CEB 50 is resiliently expandable from a contracted condition to an enlarged condition, yet biased to return towards the contracted condition. As shown in FIG. 2, the CEB 50 includes a plurality of struts 52 defining a serpentine pattern around a circumference of the CEB, each strut 52 including opposing ends that are alternately connected to adjacent struts, e.g., by curved connectors or elements 54, to define a zigzag or other serpentine pattern. In the contracted condition, the struts 52 may contact one another or otherwise minimize the cross-section of a lumen 56 extending through the CEB 50, yet may become spaced apart from one another as the CEB 50 is expanded to the enlarged condition, thereby increasing the size of the lumen 56 extending through the CEB 50, e.g., to accommodate receiving one or more devices or other structures through the lumen 56. It will be appreciated that other rings or bands may be provided for the CEB 50, e.g., a tubular mesh band that is expandable to provide a passage through the band to accommodate one or more instruments, yet resiliently compressible to close the passage upon removal of the instrument(s), as described elsewhere herein.

After the graft 10 has been implanted within a patient's body, the access ports 30 may be used to access the interior of the graft 10, e.g., during hemodialysis. Optionally, a locator device 60 may be used to identify and/or locate the access port 30 to facilitate insertion of a dialysis needle or introducer needle for an endovascular catheterization procedure. For example, each access port 30 may include a plurality of markers, e.g., ferromagnetic, echogenic, or other elements 58, e.g., surrounding or otherwise adjacent the access port 30. As shown in FIG. 1D, three magnetic elements 58 are shown spaced apart and surrounding the CEB 50.

Figure 5A:
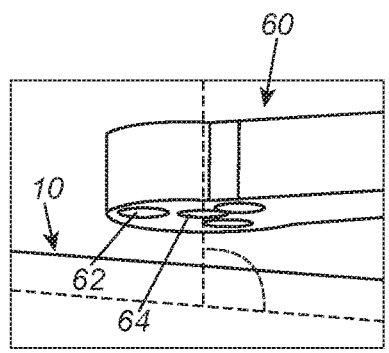
FIGS. 5A and 5B are side and top views, respectively, of an exemplary embodiment of a self-closing access port and an instrument for locating the access port.
Figure 5B:
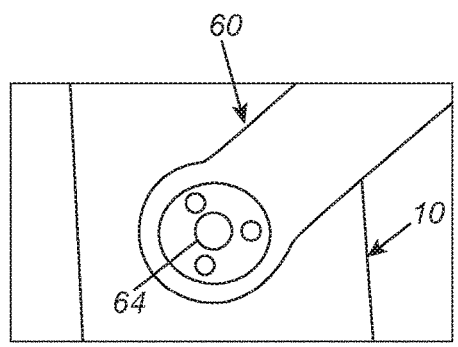
Figure 5C:
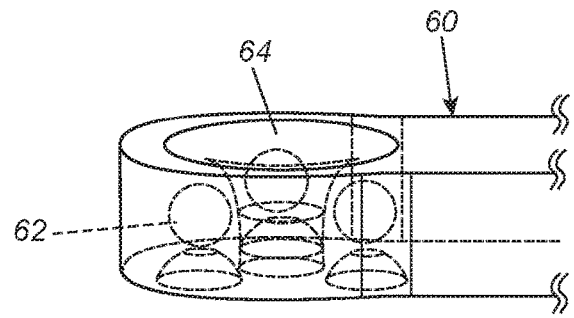
FIG. 5C is a perspective detail of the locator instrument of FIGS. 5A and 5B.

As shown in FIGS. 5A-5C, the locator device 60 may include a similar arrangement of ferromagnetic elements 62 that may correspond to the elements 58 in the access port 50. In addition, the locator device 60 may include an alignment hole 64 surrounded by the elements 62, e.g., to guide a needle or other instrument (not shown) through the access port 30, as described in the applications incorporated by reference herein. For example, the elements 58, 62 may guide the locator device 60 to align the hole 64 with the CEB 50, thereby facilitating inserting a needle through the hole 64 and the CEB 50 into the graft 10. Alternatively, the locator device 60 may include an inductance meter or other sensor (not shown) to identify and/or locate the access port 30, e.g., to identify the CEB 50 or elements 58. Optionally, as shown in FIG. 6, the locator device 60' may include a pad 66,' e.g., an antiseptic pad thereon.

Turning to FIGS. 10A-11C, another embodiment of a self-sealing access port 130 is shown that may be provided separate from a graft, blood vessel, or other tubular, curved, or substantially flat structure (not shown). The access port 130 may be attached to a body structure or otherwise implanted within a patient's body, e.g., around or otherwise onto a tubular body structure (e.g., a native or non-native, implanted tubular structure), an organ, or other tissue structure within the patient's body, as described further below. Generally, the access port 130 includes a flexible cuff, patch, or other port body 132 and a side port 140 including an elastic ring or CEB 150, e.g., surrounding or embedded in a plug 142. As best seen in FIGS. 11A-11D, the port body 132 may have a first end 132a, a second end 132b, and a generally "C" shaped or other arcuate cross-section between the first and second ends 132a, 132b, thereby defining side edges 136 extending between the first and second ends 132a, 132b, e.g., substantially parallel to a central longitudinal axis 134 of the port body 132. Alternatively, the port body 132 may be substantially flat or may have other shapes, e.g., corresponding to the shape of a tissue structure to which the access port 130 may be attached.

In an exemplary embodiment, the port body 132 may define a periphery between the side edges 136 that is greater than one hundred eighty degrees (180°), e.g., between about 180-350°, thereby providing a "cuff" that may be positioned around a tubular body structure, such as a tubular graft, fistula, and the like, as described further below. For example, as shown in FIG. 11D, the side edges 136 may be separated to open the cuff 132, e.g., to a substantially flat or larger diameter shape that facilitates positioning the port body 132 around a tubular structure. Once in position, the side edges 136 may be released, and the port body 132 may resiliently return towards its original shape, e.g., to secure or stabilize the access port 130 around the tubular structure. Alternatively, the port body 132 may define a periphery less than one hundred eighty degrees (180°) (not shown), e.g., between about 10-180°, or may be substantially flat, thereby providing a "patch" that may be attached to a wall of a tubular structure, an organ, or other tissue structure, also as described further below.

The port body 132 and side port 140 may be formed from flexible and/or substantially nonporous base material, e.g. silicone or other elastomeric material, and may be covered with fabric or other porous material 160, as shown in FIGS. 11A-11D, e.g., to promote tissue ingrowth after implantation and/or to integrate the components of the access port 130. For example, the access port 130 may be covered with a synthetic fabric 160, such as polyester, PTFE, and the like, e.g., having a porosity or internodal distance ("IND") between about forty and one hundred fifty micrometers (40-150 µm), e.g., between about sixty and one hundred micrometers (60-100 µm). In addition or alternatively, the fabric 160 may have a loose weave on one surface (or alternatively may have textured, fluffed, and/or selectively cut fibers created through a variety of mechanical methods) that better enables the base material to mechanically engage with the fibers of the fabric during the forming, molding, layering, and/or assembly process, e.g., to minimize and/or eliminate any gaps between the base material and the fabric 160.

The ring 150 may be formed from an elastic, superelastic, or shape memory material, such as a nickel-titanium alloy ("Nitinol"), that may be resiliently expanded, e.g., to accommodate receiving a needle, guidewire, catheter, introducer sheath, and the like through the side port 140, and biased to compress radially inwardly to self-seal the side port 140, similar to the CEB 50 described above.

The side port 140 may be attached to or integrally formed with the port body 132, e.g., such that the side port 140 extends transversely from an outer surface of the port body 132. For example, the side port 140 may extend substantially parallel to a transverse axis 146 defining an acute angle relative to the longitudinal axis 136, e.g., between about five and ninety degrees (5-90°), or about twenty degrees (20°). Generally, the side port 140 may include a flexible tubular or solid cylindrical plug 142 including an elastic ring 150 surrounding and/or embedded therein, e.g., to surround and/or compress the plug 142 radially inwardly on itself. Similar to the CEB 50 shown in FIG. 2, the ring 150 may include a plurality of struts 152 defining a serpentine pattern around a circumference of the ring 150, each strut 152 including opposing ends that are alternately connected to adjacent struts 152, e.g., by curved connectors or other elements 154, to define a zigzag or other serpentine pattern. Alternatively, the ring 150 may include a mesh or other interconnected strut pattern that may accommodate expansion of the ring 150 yet bias the ring 150 to return inwardly to compress the plug 142 and/or seal the side port 140.

For example, the plug 142 may be formed from silicone or other elastomeric material, e.g., by one or more of molding, casting, machining, spinning, and the like, having a desired relaxed diameter or oval shape, e.g., between about 0.1-0.5 inch (2.5-12.5 mm) or about 0.21-0.25 inch (5.25-6.25 mm). The ring 150 may be formed, for example, by laser cutting the struts 152 and connectors or elements 154 from a section of Nitinol tubing, or by cutting the struts 152 and elements 154 from a flat sheet and rolling them into a tubular shape and attaching the opposing edges. The ring 150 may be heat treated to provide a desired elasticity, e.g., allowing the ring 150 to be elastically expanded yet biased to a compress radially inwardly towards the original, relaxed diameter. For example, the ring 150 may be biased to a diameter smaller than the plug 142, and the ring 150 may be radially expanded, positioned around the plug 142, and released, whereupon the ring 150 compresses radially inwardly around the plug 142. Alternatively, the ring 150 may be biased to a diameter similar to the outer diameter of the plug 142, e.g., if the diameter of the plug 142 is slightly larger or smaller than one or more instruments likely to be inserted through the side port 140. Optionally, another layer of silicone or other material may be applied around the ring 150 and the assembly may be fused, e.g., by one or more of heating, melting, fusing, casting, and the like, and/or the plug 142 may be softened to allow the ring 150 to become embedded within the plug 142.

The port body 132 may be formed from a tubular, curved, or substantially flat body of flexible base material, e.g., formed from silicone or other elastomeric material, a substantially nonporous material, a bioabsorbable material (as described elsewhere herein), and the like, before or after forming the side port 140. For example, the side port 140 may be mounted in a mold or on a mandrel (not shown) such that a tubular body may be molded, spun, cast, or otherwise formed on one end of the side port 140, e.g., with the side port 140 defining the desired transverse angle 146. Once the tubular body is formed, it may be split or otherwise separated along its length, e.g., generally opposite the side port 140 to provide the side edges 136 shown in FIGS. 11B and 11C. Alternatively, the port body 132 may be molded, cast, or otherwise formed in a "C" or other curved shape, e.g., if the port body 132 has a periphery substantially less than 360°, or in a substantially flat shape, if desired.

It will be appreciated that the tubular, curved, or substantially flat body for the port body 132 may be formed using other methods, e.g., before or after the side port 140, and the side port 140 may be attached to the outer surface of the port body 132, e.g., before or after splitting the tubular body. For example, the side port 140 and port body 132 may be formed separately, e.g., and the side port 140 may be attached to the port body 132, e.g., by one or more of bonding with adhesive, sonic welding, fusing, and the like. Generally, the port body 132 does not include an opening over which the side port 140 is attached or otherwise formed, although, if desired, an opening may be provided (not shown), e.g., to reduce the amount of material through which a needle or other instrument must pass through the access port 130.

Once the port body 132 and side port 140 are formed and/or attached together, exposed surfaces may be covered with fabric 160, e.g., by one or more of stitching, bonding with adhesive, and the like, to provide the completed access port 130. As shown in FIGS. 11A-11D, the inner and outer surfaces, end surfaces, and the like of the port body 132, and the outer surfaces of the side port 140 are covered with one or more pieces of fabric 160, e.g., with separate pieces of fabric being stitched, bonded with adhesive, and/or otherwise attached together, as shown.

Optionally, the access port 130 (or other embodiments herein) may include one or more features to facilitate identifying and/or locating the side port 140, e.g., without direct visualization since the access port 130 may be implanted subcutaneously within a patient's body. For example, the side port 140 may extend from the port body 132 with sufficient height that the side port 140 and the access port 130 may be implanted sufficiently close to the patient's skin that the side port 140 may be identified tactilely, e.g., by palpation. Alternatively, the side port 140 may include one or more raised elements (not shown) that facilitate tactilely locating the side port 140 through the patient's skin. In addition or alternatively, the side port 140 may include one or more ferromagnetic elements that may facilitate locating the side port 140 using a magnetic locator, as described elsewhere herein, echogenic elements that may facilitate locating the side port 140 using an external ultrasound device, and the like.

The resulting access port 130 may be attached to a tubular structure, e.g., a tubular graft, fistula, blood vessel, and the like, or other tissue or body structure (not shown), e.g., before or after the tubular structure is implanted within a patient's body. For example, if the tubular structure is a graft to be implanted in a patient's body, the access port 130 may be attached to the tubular structure before introduction into the patient's body, e.g., as described below with reference to FIGS. 12A and 12B.

In a further alternative, if the tubular structure has already been implanted, created, or accessed within the patient's body, the target site may be accessed, e.g., using known procedures, and the access port 130 may be secured around or to the tubular, tissue, or body structure in situ. For example, if the port body 132 has a curved shape greater than 180°, the side edges 136 of the port body 132 may be opened and the access port 130 positioned at a desired location on the tubular structure. The side edges 136 may then be released such that the port body 132 wraps at least partially around the tubular structure, e.g., depending upon whether the periphery of the port body 132 is similar to or smaller than the circumference of the tubular structure. If the port body 132 has a curved shape less than 180° or is substantially flat, the port body 132 may simply be placed against the structure at a desired location.

Optionally, the port body 132 may be secured to the outer surface of the tubular structure, e.g., by one or more of stitching with sutures, bonding with adhesive, and the like. For example, in one embodiment, the inner surface of the port body 132 may include an adhesive or other material (not shown), which may bond to the tubular structure or another adhesive component applied to the wall of the tubular structure, for facilitating attaching or otherwise securing the port body 132 to the tubular structure. In addition or alternatively, micro-barbs or other features (not shown) may be provided on the inner surface of the port body 132, e.g., to anchor and/or otherwise enhance engagement between the port body 132 and the tubular structure.

In addition, if desired, the port body 132 may include one or more features on the first and/or second ends 132a, 132b to reduce risk of the tubular structure kinking. For example, spiral wire, axial tabs, or other features (not shown) may extend axially or circumferentially from the first and/or second ends 132a, 132b at least partially around the periphery of the port body 132. Such features may be formed from metal, such as stainless steel or Nitinol, polymers, composite materials, and the like. For example, spiral strands may extend beyond the port body 132 that may be wrapped at least partially around the tubular structure to reduce the risk of kinking immediately adjacent the access port 130.

If the port body 132 has a periphery less than one hundred eighty degrees (180°), is substantially flat, and/or is sufficiently flexible, the access port 132 may be attached to any desired structure sized to receive the port body 132 thereon. The port body 132 may have sufficient flexibility to conform substantially to the shape of the structure to which it is attached. For example, the access port 130 may be attached to the wall of a tubular structure, or to an organ, e.g., to the apex of a heart, or other tissue or body structure, to which repeated access may be desired, e.g., by one or more of suturing, bonding with adhesive, and the like. Although the access port 130 may be located subcutaneously, the side port 140 may facilitate percutaneous access into the body structure to which the access port 130 is attached.

For example, after implantation and sufficient healing, a needle (not shown) may be inserted through the side port 140, e.g., through the ring 150 to create a passage through the plug 142, and then one or more instruments may be advanced over or through the needle, e.g., a guidewire, catheter, introducer sheath, and the like. The ring 150 may resiliently expand to accommodate the instrument(s) being inserted through the side port 140 into the body structure. After completing one or more diagnostic or therapeutic procedures at one or more sites accessed via the side port 140, any instruments may be removed, and the ring 150 may resiliently compress inwardly, thereby substantially closing and/or sealing the side port 140 automatically, thereby reducing or eliminating the need to provide manual compression or other measures to reduce bleeding from the access site.

Figure 12A:
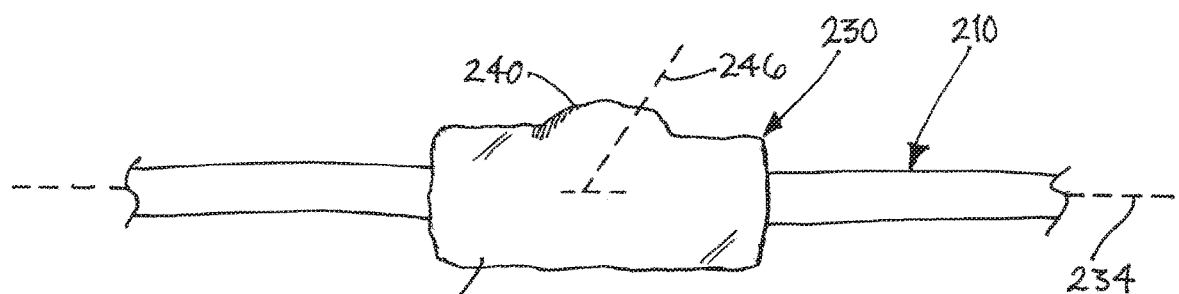
FIGS. 12A and 12B are side and top views, respectively, of a sleeve similar to the sleeve of FIGS. 10A-10C attached to a length of tubing to provide an integral access port.
Figure 12B:
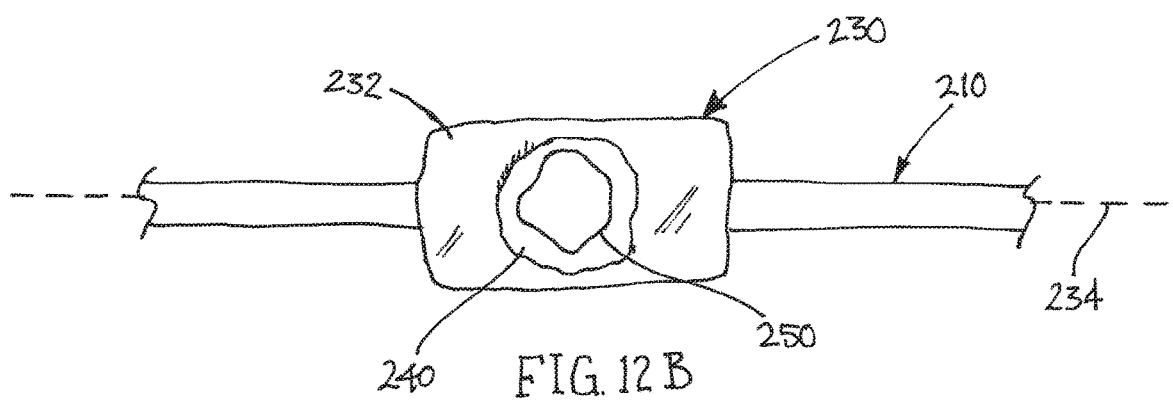

Turning to FIGS. 12A and 12B, another embodiment of an access port 230 is shown that is integrally formed on a tubular structure, such as a tubular graft 210, e.g., formed from ePTFE or other material. Generally, the access port 230 includes a port body 232, a side port 240, and a ring 250, similar to the previous embodiments. The side port 240 and ring 250 may be formed similar to methods described above, e.g., such that the ring 250 surrounds or is embedded in base material of the side port 240, and/or compresses the base material radially inwardly. The port body 232 may be integrally formed with the side port 240 and/or formed separately and attached thereto, and then the port body 232 may be split, e.g., as described above. The side edges (not shown) of the port body 232 may be separated and the access port 230 positioned around the tubular graft 210. Alternatively, the port body 232 may not be split, and the access port 230 may simply be directed over one end of the graft 210 to a desired location in an enclosed tubular configuration.

The access port 230 may then be attached to the graft 210, e.g., by one or more of bonding with adhesive, fusing, stitching with sutures, micro-barbs or other features on the inner surface, and the like. Fabric (not shown) may be stitched or otherwise attached over exposed surfaces of the access port 230 and/or graft 210 to provide a tubular graft 210 including a self-sealing access port 230 that may implanted with a patient's body together.

Turning to FIGS. 13A-14C, another embodiment of a self-sealing access port 330 is shown in the form of a cuff including a port body 332 of flexible base material defining a central longitudinal axis 336, a plurality of bands 350 surrounding or embedded within the port body 332, and fabric 360 covering exposed surfaces. The port body 332 has a generally "C" shaped cross-section including longitudinal edges 336 extending between first and second ends 332a, 332b. Alternatively, the port body 332 may be provided as a patch or other body, e.g., including a substantially planar or curved surface that may be attached to a tissue structure or other body structure, as described elsewhere herein. The port body 332 may be formed from one or more layers of flexible base material, e.g., silicone or other elastomeric or nonporous and/or flexible material, similar to the previous embodiments. In addition or alternatively, the port body 332 may be formed from bioabsorbable material, e.g., polyethylene glycol, PLA, PGA, small intestinal submucosa (SIS), and the like, as described further elsewhere herein.

The bands 350 may be formed from continuous rings or "C" shaped collars of Nitinol or other elastic, superelastic, or shape memory material formed, e.g., laser cut, mechanically cut, stamped, machined, and the like, from a tube, wire, or sheet, similar to the CEB 50 and other embodiments herein. Each band 350 may extend at least partially around the periphery of the port body 332 transverse to the longitudinal axis 336. For example, each band 350 may include a plurality of longitudinal struts 352 defining a serpentine pattern around a periphery of the port body 332, each strut 352 including opposing ends that are alternately connected to adjacent struts 352 by curved circumferential connectors, struts, or elements 354, e.g., to define a zigzag or other serpentine pattern. The longitudinal struts 352 may extend substantially parallel to the longitudinal axis 334 or, alternatively, may extend diagonally or helically relative to the longitudinal axis 334 (not shown).

Alternatively, the access port 330 may include a contiguous mesh or other enclosed or open pattern including struts at least partially surrounding openings (not shown) through which one or more instruments may be inserted, as described further elsewhere herein. For example, individual bands or a substantially continuous mesh sheet may be provided that include interconnected struts defining generally diamond-shaped or other enclosed openings therebetween (not shown), with the struts being separable to increase the size of the openings, e.g., to accommodate receiving one or more instruments therethrough, as described elsewhere herein. Exemplary mesh patterns that may be used are shown in U.S. Pat. Nos. 4,733,665, 5,344,426, and 5,591,197 the entire disclosures of which are expressly incorporated by reference herein. In further alternatives, the access port 330 may include one or more wires or other elongate filaments wound helically or otherwise around the port body 332 and/or along a desired length of the port body 332, e.g., a single helical element, multiple helical filaments braided or otherwise wound together into a mesh, and the like.

In a further alternative, struts or bands may extend axially along a length of the access port 330 (not shown). For example, a plurality of substantially straight wires or other filaments may be embedded within or otherwise fixed to the base material. The filaments may be spaced apart sufficiently to accommodate inserting one or more instruments (not shown) through the access port 330, with the filaments moving laterally to accommodate the instrument(s) passing therethrough and resiliently returning to their original configuration to substantially seal the access port 330, similar to other embodiments herein. Alternatively, the filaments may include a zigzag or other pattern that extends transversely while the filaments extend generally axially between the ends of the access port 330. Further, the filaments or struts may impose a substantially continuous compressive force on the adjacent base material, which may enhance sealing any passages created through the base material, similar to other embodiments herein.

Figure 13A:
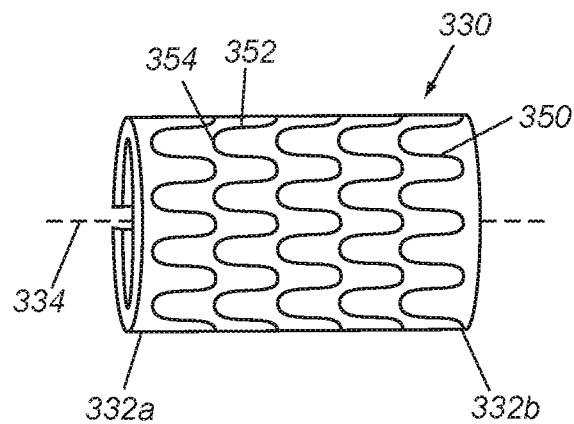
FIG. 13A is a side view of a silicone sleeve including a plurality of rings including separable struts embedded therein.
Figure 13B:
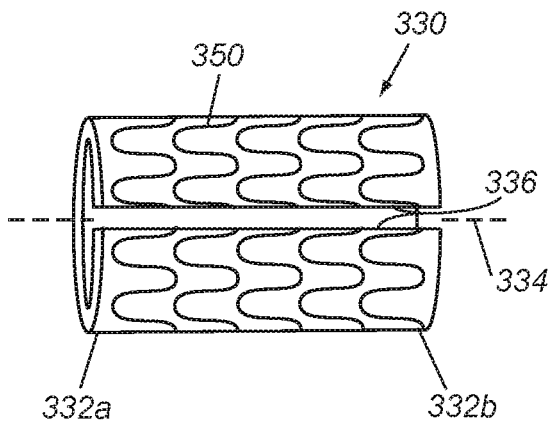
FIG. 13B is a side view of the silicone sleeve of FIG. 13A split along a length of the sleeve.

The struts, filaments, or features of the bands or mesh, e.g., the struts 352 and curved connectors 354 shown in FIGS. 13A and 13B, may have any desired cross-section. For example, the features may have generally round, elliptical, rectangular, or square cross-sections, optionally, having tapered or rounded surfaces to facilitate passing an instrument between the features. For example, the features may be formed with a rectangular cross-section that may have rounded or tapered edges, e.g., by one or more of electro-polishing, machining, laser cutting, and the like. Optionally, the features may have a thickness (extending radially relative to the central longitudinal axis 336) that is greater than their width (extending axially and/or circumferentially), which may provide increased radial support yet accommodate separation of the features "laterally," as described further elsewhere herein.

In the embodiment shown in FIGS. 13A and 13B, each band 350 has a generally cylindrical shape, e.g., including first and second longitudinal ends that are spaced apart axially from one another and aligned around the periphery of the port body 332, e.g., substantially perpendicular to the longitudinal axis 334. Alternatively, the bands 350 may extend helically around the periphery of the port body 332 (not shown) and/or may have other shapes or configurations including an axial length dimension along a length of the port body 332 and a peripheral dimension extending at least partially around the periphery of the port body 332.

The bands 350 may be disposed immediately adjacent one another, e.g., with adjacent bands 350 in phase with one another. For example, as shown in FIGS. 13A and 13B, the curved connectors 354 on the first end of a first band 350 may be disposed between the curved connectors 354 on the second end of an adjacent band 350. Alternatively, adjacent bands 350 may be spaced axially apart from one another (not shown), thereby providing an unreinforced annulus of the port body 332 between adjacent bands 350, which may accommodate introducing relatively large instruments between the struts 352 and/or bands 350, as described further below. In another alternative, portions of adjacent bands may overlap one another (not shown) or a braided or other multiple layer mesh may be provided (also not shown), as long as struts or other elements of the mesh are free to move laterally and/or resiliently to accommodate one or more instruments through openings between the elements.

In a further alternative, adjacent bands 350 may be out of phase with one another, e.g., such that the curved connectors 354 of adjacent bands 350 are disposed adjacent one another, e.g., aligned axially or diagonally relative to one another (not shown). In this alternative, adjacent bands may define openings surrounded by pairs of struts from each adjacent band, which may accommodate receiving relatively large instruments through the openings yet substantially closing the openings once the instrument(s) are removed. Optionally, one or more of the curved connectors 354 on a band 350 may be coupled to one or more curved connectors 354 of an adjacent band 350. For example, adjacent curved connectors 354 may be coupled directly together, or may be coupled by a flexible link (not shown), e.g., to limit movement of adjacent bands 350 relative to one another.

Turning to FIG. 13A, the access port 330 may be formed by initially creating a tubular body of silicone, PET, or other flexible, nonporous, and/or bioabsorbable base material having a desired length and/or diameter for the port body 352, e.g., by one or more of molding, casting, machining, spinning, and the like. For example, the tubular body may have a length between about one and ten centimeters (1-10 cm), a diameter between about one and forty millimeters (1-40 mm), and a wall thickness between about 0.5 and five millimeters (0.5-5.0 mm).

The set of bands 350 may be formed individually or simultaneously, e.g., by laser cutting from a tube, winding one or more strands in a zigzag or other circuitous pattern around a mandrel, and the like. For example, a length of Nitinol wire or other material may be wound around a cylindrical mandrel (not shown) between posts to define a zigzag or other circuitous pattern to define an enclosed band (or entire set of bands) or may be wound helically along a mandrel to define a substantially continuous helical band. Alternatively, a single tube may be cut to create the set of bands 350 or a substantially continuous mesh of struts (not shown), as desired. The individual or set of bands 350 may have lengths between about three and one hundred twenty five millimeters (3.0-125 mm), e.g., coextensive with or less than the length of the port body 352.

Alternatively, the bands 350 may be formed from a flat sheet, e.g., by one or more of laser cutting, mechanically cutting, etching, stamping, and the like, one or more sets of struts and connectors from the sheet, and then rolling the sheet. The longitudinal edges of the rolled sheet may remain separate, e.g., to provide "C" shaped bands, or alternatively the longitudinal edges may be attached together, e.g., by one or more of welding, soldering, fusing, bonding with adhesive, and the like, to provide an enclosed band. In a further alternative, a set of bands 350, e.g., providing an entire set for the access port 330, may be formed simultaneously from a tube or sheet, particularly if the bands 350 are connected together, e.g., by links or directly by adjacent connectors 354.

The bands 350 may be heat treated and/or otherwise processed to provide a desired finish and/or mechanical properties to the bands 350. For example, the bands 350 may be heat treated such that the bands 350 are biased to a desired relaxed diameter, e.g., substantially the same as or smaller than the tubular body for the port body 332, yet may be resiliently expanded and/or have one or more struts 352 and/or curved connectors 354 resiliently deformed to accommodate receiving a needle or other instrument (not shown) between adjacent struts 352, connectors 354, and/or bands 350, as described further below. Alternatively, if the bands 350 are formed from a sheet of material, the sheet may be heat treated and/or otherwise processed to provide the desired shape and/or properties for the bands 350 formed from the sheet.

In an exemplary embodiment, for Nitinol material, the bands 350 may be heat treated such that the $A_f$ temperature for the material is less than body temperature (about 37° C.), e.g., between about ten and thirty degrees Celsius (10-30° C.). For example, the Nitinol material may remain substantially in an Austenitic state when the access port 330 is implanted within a patient's body, yet may operate within a superelastic range, e.g., transforming to a stress-induced martensitic state when an instrument is inserted through the openings in the access port 330, as described elsewhere herein. Alternatively, the Nitinol material may be heat treated to take advantage of the temperature-activated or other shape memory properties of the material. For example, the material may be heat treated such that the bands 350 are substantially martensitic at or below ambient temperature, e.g., below twenty degrees Celsius (20° C.), such that the bands 350 may be relatively soft and/or plastically deformable, which may facilitate manipulation, introduction, or implantation of the access port 330. At around body temperature, e.g., at thirty seven degrees Celsius (37° C.) or higher, the bands 350 may be substantially austenitic, e.g., to recover any desired shape programmed into the material and to provide elastic or superelastic properties to the bands 350 once the access port 330 is implanted within a patient's body.

With continued reference to FIG. 13A, to form the access port 330, a set of bands 350 may be fixed to, e.g., placed on, bonded to, or embedded in, the tubular body or other base material of the port body 332. For example, in their relaxed state, the bands 350 may have a diameter smaller than the base material of the port body 332, and the bands 350 may be expanded radially outwardly, positioned around the tubular body, and released such that the bands 350 apply a radially inward compressive force against the tubular body. Such compression may be sufficient to bias the port body 332 to a desired diameter, e.g., smaller than a tubular body to which the access port 330 may be secured, for example, to reduce migration and/or otherwise secure the access port 330. In addition, such compression may impose a substantially continuous compressive force on the port body 332, which may enhance the self-sealing function of the access port 330. Alternatively, the bands 350 may be biased to a diameter similar to the outer surface of the tubular body such that the bands 350 surround the tubular body without substantial radially inward compression. In this alternative, the bands 350 may remain in a substantially relaxed state and/or may not apply a radially inward compressive force against the base material of the port body 332

Optionally, the bands 350 may be expanded "laterally" in addition to or instead of being radially expanded. For example, the bands 350 may be expanded from a relaxed state to increase the spacing of the struts or filaments, i.e., increase the size of the openings defined by the bands 350, and then placed on, embedded in, and/or otherwise attached to the base material of the port body 332. In this embodiment, once the bands 350 are fixed to the port body 332, the bands 350 may be released such that the bands 350 are biased to return laterally inwardly towards the relaxed state, thereby biasing the struts and openings to a smaller size, yet accommodating the struts moving laterally to accommodate an instrument being inserted through the openings, as described elsewhere herein.

As described above, once fixed to the port body 332, the bands 350 may be spaced apart from, may contact, may overlap, or may be nested between adjacent bands 350, e.g., in phase or out of phase with one another, as desired. Alternatively, if the bands 350 are connected to one another, the entire set of bands 350 may be positioned around the tubular body with or without expanding and releasing the bands.

Optionally, with the bands 350 surrounding, placed against, or fixed relative to the base material of the port body 332, another layer of silicone, PET, or other flexible base material may be applied around the bands 350 to further form the port body 332, thereby embedding the bands 350 within the base material. For example, an outer layer of silicone may be applied around the bands 350 and the assembly may be heated, cured, or otherwise processed to fuse, melt, or otherwise bond the material of the outer layer to the bands 350 and/or the material of the tubular body. Alternatively, the tubular body may be softened or otherwise treated to allow the bands 350 to become embedded therein, or the tubular body may be formed around the bands 350, if desired. In a further alternative, the bands 350 may be secured around the tubular body, e.g., by one or more of bonding with adhesive, sonic welding, fusing, and the like.

As shown in FIGS. 13A and 13B, a plurality of bands 350 are embedded in or secured around the port body 332, e.g., two, three, four, five (as shown), or more bands 350, as desired. For example, as shown, the bands 350 may be provided along substantially the entire length of the port body 332. Alternatively, the bands 350 may be provided only in a central region of the port body 332, e.g., with regions adjacent the first and second ends 332a, 332b including unsupported silicone or other base material (not shown). In this alternative, the bands 350 may provide a self-sealing or self-closing access region only along the central region with the unsupported end regions providing a transition, e.g., to reduce kinking and the like when the access port 330 is attached to a tubular structure. The unsupported end regions may have substantially uniform properties similar to the central region or may have different properties. For example, the end regions may have a tapered thickness, e.g., relatively thick immediately adjacent the central region and tapering towards the ends of the port body 332, may be formed from a relatively softer durometer material, and the like.

In a further alternative, the access port may include multiple regions embedded with or otherwise supported by bands that are separated by unsupported regions of the port body (not shown). Thus, in this alternative, a self-sealing cuff or patch may be provided that includes multiple spaced-apart self-closing access regions separated by unsupported regions.

Returning to FIGS. 13A and 13B, once the bands 350 are embedded within or otherwise secured to the port body 332, the port body 332 may be split or otherwise separated, e.g., by one or more of laser cutting, mechanical cutting, and the like, through the silicone material and the bands 350, to provide the side edges 336, as shown in FIG. 13B. Alternatively, the bands 350 may be formed as discontinuous "C" shaped collars that may be attached around or embedded within the port body 332 before or after splitting the port body 332 to create the longitudinal edges 336. In a further alternative, a length of base material with embedded bands corresponding to multiple individual access ports may be formed using the methods described above, and the resulting assembly may be cut or otherwise separated into individual port bodies 332, if desired. In yet a further alternative, the bands and port bodies may not be cut longitudinally, if a tubular access port is desired, similar to other embodiments herein.

Figure 14A:
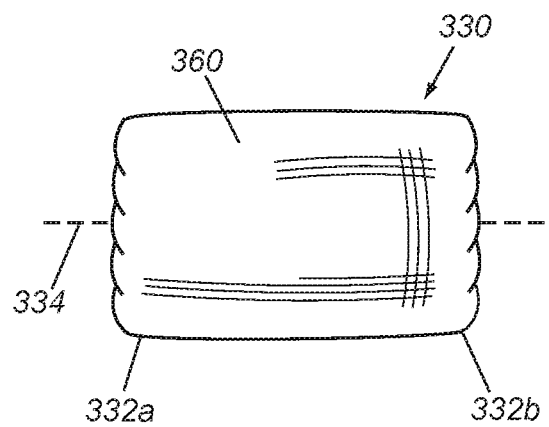
FIGS. 14A-14C are top, bottom, and end views, respectively, of the sleeve of FIG. 13B covered with fabric to provide a cuff with integral penetrable, self-sealing access port.
Figure 14B:
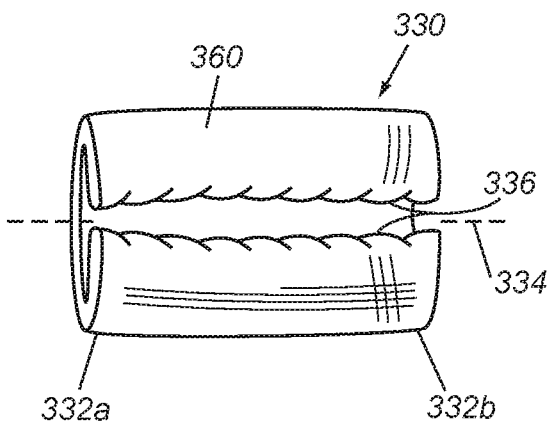
Figure 14C:
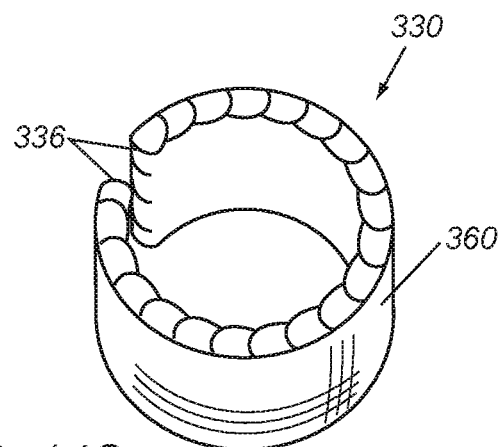
Figure 15:
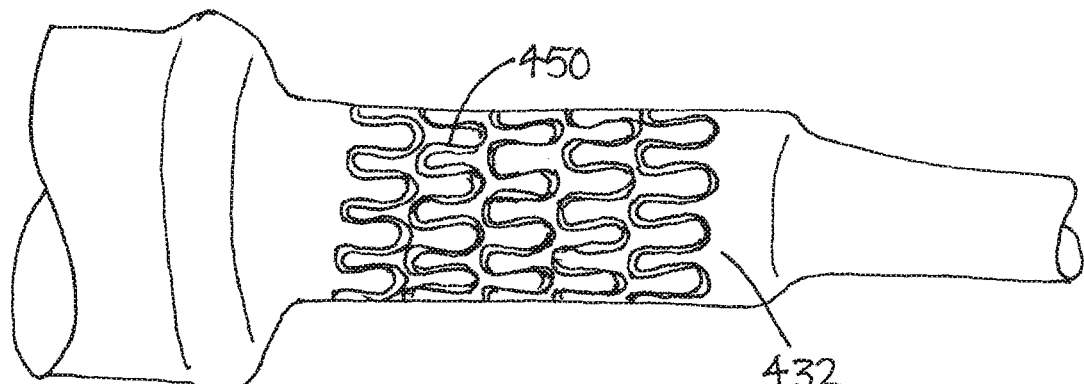
FIG. 15 is a side view of a length of silicone tubing including a plurality of zigzag rings embedded therein.
Figure 16A:
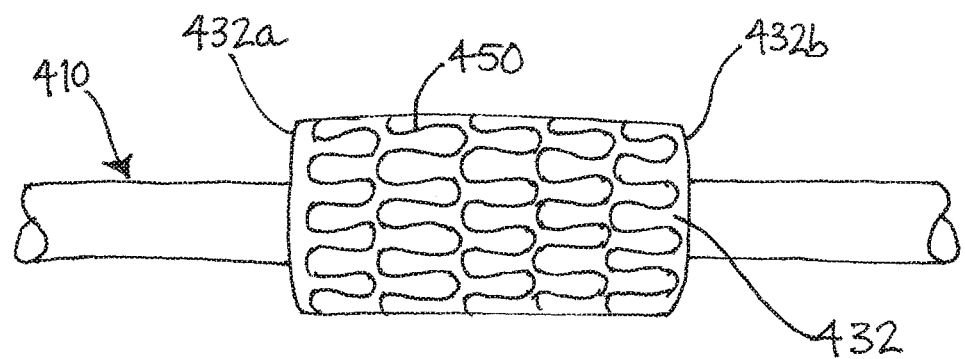
FIGS. 16A and 16B are top and bottom views, respectively, of a silicone sleeve created from the silicone tubing of FIG. 15, split along its length, and attached onto a length of tubing.
Figure 16B:
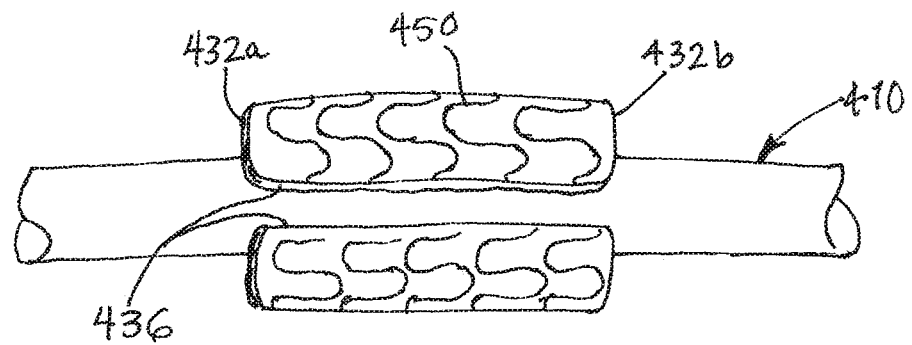

Turning to FIGS. 14A-14C, fabric 360 may be applied over any exposed surfaces, e.g., over the outer, inner, and end surfaces of the port body 332 to provide the completed access port 330. For example, one or more pieces of fabric 160 may be wrapped around the port body 332 and stitched together and/or to the port body 332, e.g., similar to other embodiments herein. Optionally, the access port 330 may include one or more tactile elements, ferromagnetic elements, echogenic elements, and the like (not shown), e.g., to facilitate locating the access port 330 and/or bands 350 when the access port 330 is implanted subcutaneously or otherwise within a patient's body.

During use, the access port 330 may be positioned around a tubular structure, e.g., a graft before or after implantation, a blood vessel, fistula, or other tubular structure (not shown) exposed or otherwise accessed within a patient's body. For example, the side edges 336 may be separated, and the port body 332 positioned around or otherwise adjacent a tubular structure. The side edges 336 may be released to allow the port body 332 to resiliently wrap at least partially around the tubular structure and/or the port body 332 may be attached to the tubular structure, e.g., by one or more of bonding with adhesive, suturing, fusing, and the like. Alternatively, if the access port includes an enclosed tubular port body (not shown), the access port may be directed over a tubular structure from one end thereof (which may be preexisting or may be created by cutting the tubular structure).

In an alternative embodiment, an access port similar to access port 330 may be attached to a tubular graft or other structure before introduction and/or implantation within a patient's body. In another alternative, the access port 330 may be integrally formed into the wall of a graft, e.g., during manufacturing of the graft, if desired. For example, rather than providing a separate port body 332, the bands 350 or other support elements may be integrally molded or otherwise embedded within a wall of a tubular graft or other implant. Thus, the implant may include an integral access port that operates similar to the other embodiments herein.

Figure 20B:
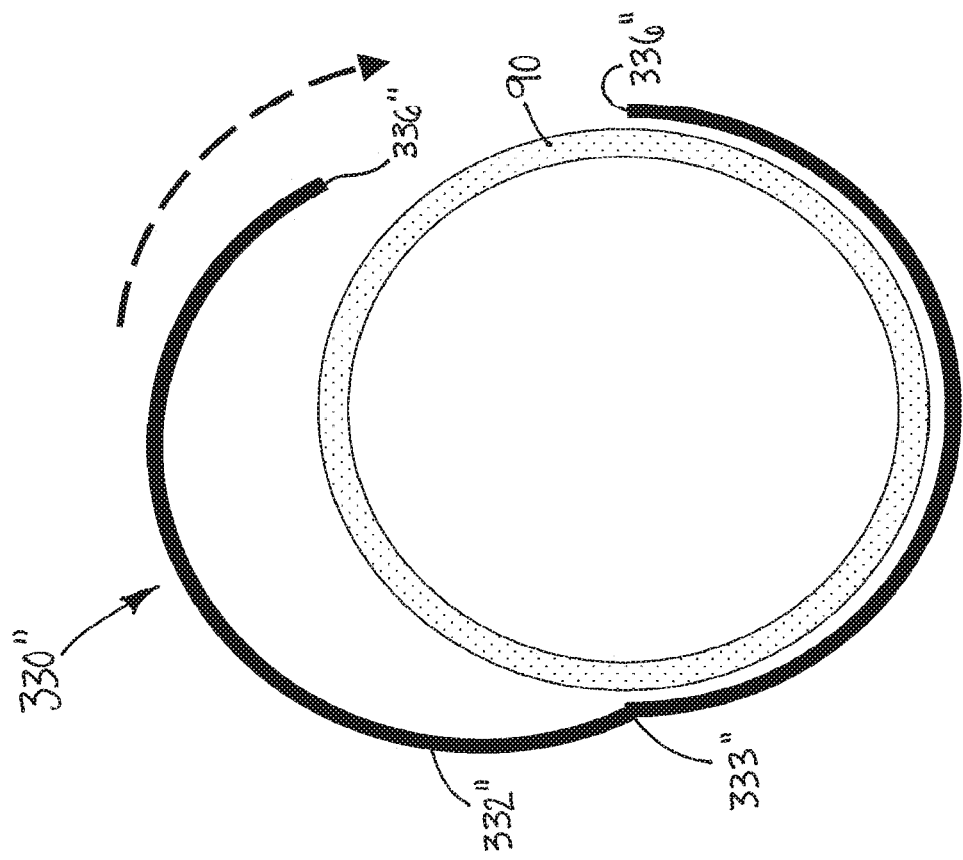
FIGS. 20A and 20B are cross-sectional views of alternative embodiments of cuffs being attached around a tubular body structure.
Figure 20A:
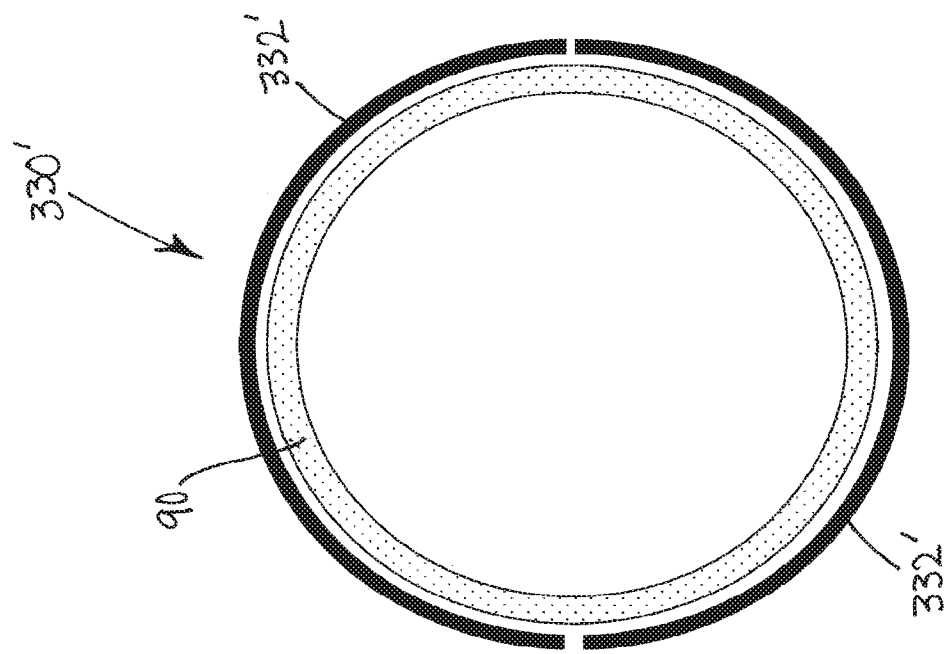

In an alternative embodiment, shown in FIG. 20A, an access port 330' may be provided that includes a plurality of separate port bodies 332' that may be placed around a vessel or other tubular structure 90. For example, as shown, the access port 330' includes a pair of port bodies 332' including bands or other support elements (not shown) that surround the vessel 90, e.g., in a clamshell type configuration. The port bodies 332' may be attached to the vessel 90 separately or may include one or more cooperating connectors, e.g., hinged elements, sutures, and the like (not shown), that attach the adjacent edges of the port bodies 332' together. In a further alternative, shown in FIG. 20B, an access port 330" is shown that includes a port body 332" having a hinged region 333." Thus, the port body 332" may be opened along its length, placed around the vessel 90, and then closed such that the side edges 336" are disposed adjacent one another. The side edges 336" may be spaced apart from one another, contact one another, or overlap one another, if desired, and/or may include one or more connectors (not shown) for securing the side edges 336" relative to one another, if desired.

In either of these embodiments, the access port 332,' 332" may have a diameter similar to the outer diameter of the vessel 90 or may have a slightly smaller diameter if it is desired to apply a radially compressive force to the vessel 90. The access ports 332,' 332" may be attached to the vessel 90, e.g., by one or more of stitching with sutures, bonding with adhesive, and the like, similar to other embodiments herein. Optionally, micro-barbs or other features (not shown) may be provided on the inner surfaces of the port bodies 332' similar to other embodiments herein.

Alternatively, the port bodies 332,' 332" may be provided as rectangular, substantially flat or otherwise sufficiently flexible sheets that may simply be wrapped around a vessel 90 and secured thereto, e.g., by bonding, suturing, or clipping the port bodies 332,' 332" to the vessel 90 and/or to secure the ends of the port bodies 332,' 332" to one another. The resulting access ports 332,' 332" may substantially surround the entire circumference of the vessel 90 and/or partially overlap, which may reduce the risk of leakage from the vessel 90, e.g., due to over-penetration, e.g., if a needle is directed into one side and accidentally out the other side of a vessel, as described elsewhere herein.

Returning to FIGS. 14A-14C and with reference to the access port 330 (although the description may apply equally to other embodiments herein), if it is desired to access a lumen of the tubular structure, a needle (not shown) may be introduced through the patient's skin over the access port 330, and directed through the port body 332 into the lumen. The thickness of the access port 330 may facilitate identifying the ends of the access port 330, e.g., by palpation, since the ends may be identified tactilely relative to the adjacent regions of the tubular structure. Thus, the access port 330 may reduce the risk of accidental sticks in regions of the tubular structure not covered by the access port 330. Optionally, similar to other embodiments herein, the access port 330 may include one or more locator elements (not shown), which may be identified by an external probe, e.g., a magnetic or ultrasound device, to facilitate identifying the location of the access port 330.

As the needle is inserted, if the needle encounters any of the struts 352, connectors 354, or other features of the bands 350, the encountered features may resiliently move away from the needle to create a passage through the access port 330 into the lumen. If one or more larger instruments are subsequently introduced through the access port 330, e.g., over a guidewire advanced through the needle or over the needle itself, the struts 352, connectors 354, and/or other features of the bands 350 may resiliently separate to create a sufficiently large passage through the port body 332 to accommodate the instrument(s). Generally, the struts 352, connectors 354, and/or other features of the bands 350 separate "laterally," i.e., circumferentially and/or axially within the cylindrical surface defined by the port body 332, to provide a passage through the port body 332. As used herein, "laterally" refers to movement of the features of the bands 350 or other mesh substantially in a direction around the circumference and/or along the length of the port body 332 within the base material and generally not out towards the inner or outer surfaces of the port body 332 (i.e., "within the plane" of the port body 332). For example, if the port body 332 were substantially flat within a plane, laterally would refer to movement of the features of the bands substantially within the plane and generally not out of the plane towards the inner or outer surfaces.

Optionally, the material of the port body 332 may include one or more surface features to facilitate penetration of a needle or other instrument through the access port 330. For example, the port body 332 may have a variable thickness, e.g., defining valleys and ridges along its outer surface (not shown), with the ridges overlying struts or other features of the bands 350 and the valleys disposed between the features of the bands 350. When a needle or other instrument (not shown) is inserted through the access port 330, the ridges may guide the tip of the needle into the regions between the struts of the bands 350, e.g., to reduce the risk of interference between the needle and the bands 350.

After a procedure is completed via the access port 330 and the lumen of the tubular structure, any instruments may be removed, whereupon the bands 350 may resiliently return towards their original shape, e.g., laterally inwardly towards their original configuration, thereby compressing the material of the port body 332 to close any passage created therethrough. Thus, the bands 350 may provide a self-sealing or self-closing feature that automatically substantially seals any passages created through the port body 332 by a needle or other instruments.

For example, if the spacing of the struts or other features of the bands 350 is smaller than the cross-section of the instrument(s) inserted through the access port 330, the features may separate to create a passage through the access port 330 that is larger than the spacing of the features in their relaxed state. However, even if the spacing of the features is larger than the cross-section of the instrument(s) inserted through the access port 330, the bands 350 may provide sufficient bias within the plane of the port body 332 to bias the port body material to resiliently close laterally inwardly around any passage created therethrough to automatically close the passage. Thus, the elasticity/bias of the bands 350 may reinforce and/or bias the material of the port body 332 to allow repeated access through the access port 330, while automatically closing any passages to self-seal the access port 330. The bias or support of the port body material between the struts of the bands 350 may also reduce the risk of the material breaking down over time due to multiple penetrations.

One of the advantages of the access port 330 is that a needle or other instrument may be introduced at multiple locations through the port body 332, unlike the access ports 130, 230. As long as the needle is inserted through a region of the access port 330 including and/or supported by one or more bands 350, the features of the bands 350 may separate or otherwise open to accommodate the needle and resiliently return towards their substantially stress free or preloaded original configurations when all instruments are removed. Thus, in this embodiment, there may be no need for locator elements (unless provided to facilitate identifying the ends of the access region), or a single access region may provide multiple access sites, rather than having to implant multiple discrete access ports.

In addition, such bands 350 may protect the accessed tubular structure from over-penetration of needles or other instruments. For example, if the access port 330 substantially surrounds the tubular structure, a needle or other instrument that is inadvertently inserted into one side of the access port 330 through the entire tubular structure and out the opposite side of the access port 330 may be removed without substantial risk of bleeding or other leakage from the posterior location as well as the anterior location since the access port 330 may self-seal both openings.

Optionally, if the port body 332 has a periphery defining less than one hundred eighty degrees (180°) or is substantially flat, the access port 330 may be applied as a patch to the surface of any body structure, e.g., a tubular structure, such as a graft, fistula, blood vessel, and the like, or to an organ, abdominal wall, or other tissue structure. The "patch" may have a variety of shapes and/or sizes depending upon the application and/or may have sufficient flexibility to conform to the shape of anatomy to which the patch is applied. For example, the port body 332 may have a two-dimensional shape, e.g., a rectangular, square, oval, or circular shape, with bands 350 provided along the entire surface area of the port body 332 or spaced apart inwardly from an outer perimeter of the "patch." Such patches may be created by cutting or otherwise separating a desired shape from the tubular body described above after embedding or securing bands thereto. Alternatively, individual patches may be created by embedding or securing flat bands to patches of silicone or other base material formed into the desired shape.

In a further alternative, the patch may be created by laminating multiple layers of material to create a self-sealing structure that may be attached to a tissue structure. For example, each layer may include elastic support elements, e.g., a mesh, struts, and the like, that support one or more layers of base material within a plane of the base material(s). Alternatively, one or more layers of base material may be provided that has sufficient flexibility and bias such that the support elements may be omitted.

The resulting patch may accommodate creating an opening through the base material(s) of the layers when one or more instruments are inserted through the patch, i.e., with the support elements moving laterally within the plane of the base material(s). After removing the instrument(s), the support elements may bias the base material(s) of the respective layers laterally towards their original configuration, thereby automatically closing the opening.

Alternatively, the access port 330 may be provided in a three-dimension configuration, e.g., a conical, parabolic, or other shape (not shown). In addition or alternatively, the access port 330 may be provided in a curved cylindrical (e.g., substantially uniform or tapered) or other shape having a desired arc length, e.g., up to sixty degrees (60°), one hundred twenty degrees (120°), or between five and three hundred sixty degrees (5-360°), or between one hundred eighty and three hundred sixty degrees (180-360°), and the like. The port body 332 may be biased to a predetermined three-dimensional shape yet sufficiently flexible to accommodate the actual anatomy encountered, e.g., having one or more bands or other structures including elastic struts embedded within or otherwise secured to a flexible base material, such as silicone or other elastomer, similar to other embodiments herein.

Optionally, the access port 330 may be used as a patch or surgical mesh, e.g., which may be attached or otherwise secured to weakened areas of tissue or organs to provide reinforcement in addition to allowing subsequent access, if desired. For example, the access port 330 may be applied as a patch for vascular repair, e.g., over a pseudo-aneurysm, or after excising a pseudo-aneurysm to reinforce the region and/or allow subsequent access.

Figure 18:
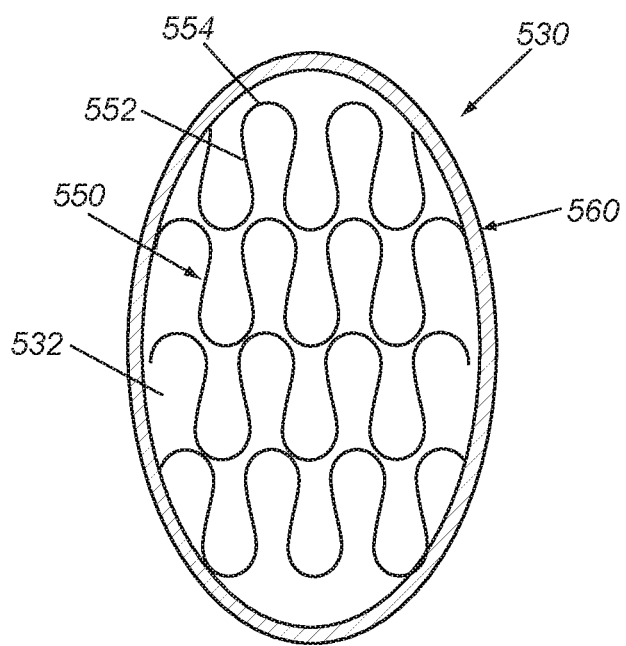
FIG. 18 is a top view of an exemplary embodiment of a reinforced patch including elastic support elements embedded in a base material and surrounded by a sewing ring.

Turning to FIG. 18, an exemplary embodiment of a surgical patch 530 is shown that includes one or more layers of base material 532, e.g., defining a substantially flat or curved "plane," and a plurality of support elements or bands 550 embedded or otherwise attached to the base material 530. For example, the base material 532 may include one or more layers of silicone or other elastomeric material that may be biased to a flat or curved planar shape or may be "floppy," i.e., may have no particular shape and may conform substantially to any desired shape. As shown, the support elements include a plurality of bands 550 including features, e.g., struts 552 alternately connected by curved connectors 554, similar to other embodiments herein. The bands 550 may extend along a substantially linear axis across the base material 532, e.g., defining a sinusoidal or other alternating pattern, adjacent to and substantially parallel to one another. Thus, the features, e.g., struts 552 and connectors 554, may support the base material 532, such that the support elements 550 may be separable laterally to accommodate receiving one or more instruments (not shown) through the base material 532, yet resiliently biased to close any openings through the base material 532 created by the instrument(s), similar to other embodiments herein.

Alternatively, the patch 530 may include one or more layers of base material 532 without the support elements 550 covered with fabric or other material (not shown). The base material 532 may be constructed to be self-supporting and resiliently biased to allow the creation of passages therethrough by a needle or other instrument (not shown), yet self-close the passage(s) upon removal of the instrument(s) to prevent substantial leakage through the patch 530. For example, each layer of base material may provide axial strength in a desired axial direction, and multiple layers may be attached together with the axial directions orthogonal or otherwise intersecting one another. The direction of axial strength may be achieved by selection of the polymer or other material for the base material or by embedding strands, wires, or other axial elements within the base material (not shown). Similar to other embodiments herein the patch 530 may be biased to a substantially flat configuration, a curved configuration, or may be "floppy," as described elsewhere herein.

In addition, as shown in FIG. 18, the surgical patch 530 may include a sewing ring or cuff 560 extending around a periphery of the base material 532, e.g., to facilitate securing the patch 530 to tissue, as described further below. For example, the sewing ring 560 may include one or more layers of fabric or other material, e.g., optionally filled with foam, fabric, or other resilient, flexible, and/or penetrable material, attached to the periphery of the base material 532, e.g., by stitching with sutures, bonding with adhesive, and the like. The base material 532 may also be covered with fabric or other material, e.g. the same or different material than the sewing ring 560, to enhance tissue ingrowth and/or integrate the components of the patch 530.

The patch 530 may have a generally round shape, e.g., an elliptical, oval, or substantially circular shape. Alternatively, the patch 530 may have a square or other rectangular shape, or other geometric shape, as desired.

In an alternative embodiment, the patch 530 may be provided in a "cut-to-length" configuration, e.g., an elongate sheet or roll (not shown) of base material 532, having a predetermined width and a length sufficient to provide multiple individual patches. In this alternative, the sewing ring 560 may be omitted or may be provided along the longitudinal edges of the sheet or roll. Optionally, the sheet or roll may include weakened regions to facilitate separating individual patches or may include unsupported regions without support elements 550 between regions with support elements 550, e.g., that may be easily cut otherwise separated to allow individual patches to be separated from the sheet or roll.

Figure 19A:
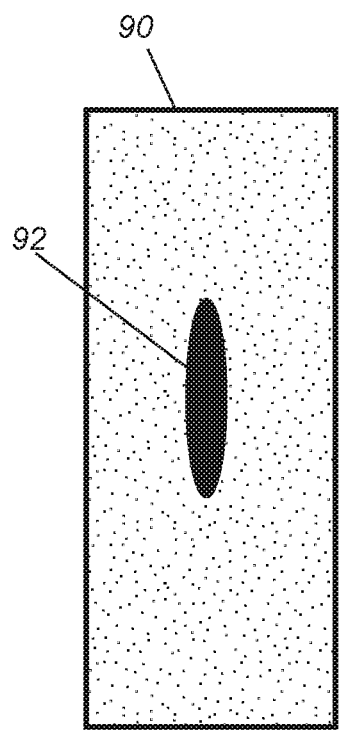
FIGS. 19A-19C are top views of a wall of a vessel, showing a method for repairing the wall using the patch of FIG. 18.
Figure 19B:
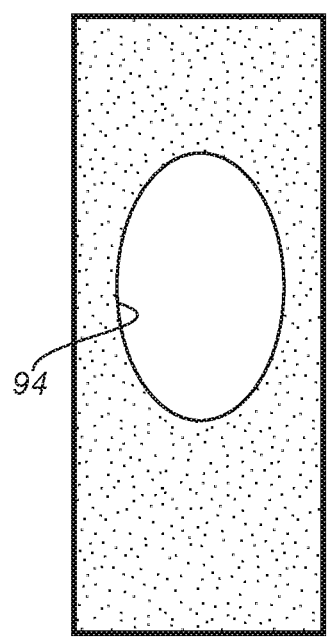
Figure 19C:
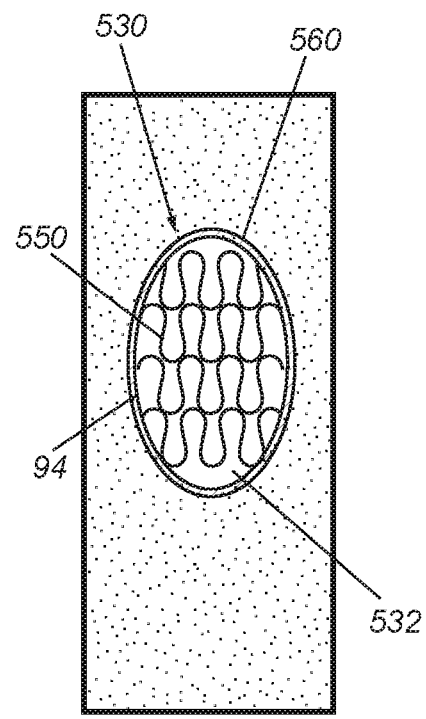

Turning to FIGS. 19A-19C, an exemplary method is shown for vascular repair using the patch 530 of FIG. 18. As shown in FIG. 19A, a blood vessel 90 may include a weakened region 92 in need of repair. Turning to FIG. 19B, the weakened region 92 and adjacent tissue may be resected to create an opening 94, e.g., corresponding to the size and shape of the patch 530. The patch 530 may then be attached within or over the opening 94, e.g., by suturing the sewing ring 560 to the vessel wall surrounding the opening 94. Alternatively, the patch 530 may be attached to the wall of the vessel 90 without removing the weakened region 92, e.g., by attaching the patch 530 to the vessel 90 over the weakened region 92 or within the lumen underlying the weakened region 92, thereby supporting the weakened region 92. In another alternative, the patch 530 may be attached to a vessel wall that does not include a weakened region, e.g., as a prophylactic measure to prevent a weakened region from developing at the site of implantation. The patch 530 may thereafter provide a structure for supporting the vessel wall and/or provide a self-closing structure allowing multiple access to the vessel 90, similar to other embodiments herein.

In another embodiment, an access port patch may be attached to the apex of the left ventricle of a heart to facilitate trans-apical procedures, e.g., aortic valve replacement, and the like. Such a patch may allow one-time or repeated access through the LV apex into the left ventricle. Once the procedure is completed, any instruments introduced through the patch may be removed, and the patch may provide substantially instantaneous sealing of the LV apex.

In another option, the access port 330 may be provided in a tubular or "C" shaped configuration, and may be introduced into a blood vessel or other body lumen. For example, the access port 330 may be rolled or otherwise compressed, and loaded into a catheter, delivery sheath, and the like (not shown). Alternatively, the access port 330 may be advanced over a needle, e.g., a dialysis needle, into the interior of a graft, fistula, or other tubular structure after dialysis. Once deployed within a lumen of a tubular structure or body lumen, the access port 330 may be attached to the wall of the body lumen, e.g., by one or more of stitching with sutures, bonding with adhesive, interference fit due to the radial bias of the access port 330, and the like. Thus, the access port 330 may provide an immediate barrier to leakage through a wall of the body lumen, e.g., to substantially seal a puncture site from the interior of the body lumen. In addition, the access port 330 may allow the lumen to be subsequently accessed again, as desired, with the access port 330 providing a self-sealing access region, similar to other embodiments herein.

Optionally, the access port 330 may be biased to expand to a diameter larger than the body lumen within which it is implanted. For example, in dialysis patients in which an AV fistula is created, it may be desirable to remodel, e.g., expand, the native vein attached to an artery to create the fistula. If the access port 330 is biased to a diameter larger than the existing vein, e.g., similar to the diameter of the artery, the access port 330 may apply a radially outward and/or circumferential force against the surrounding wall of the vein. This bias may accelerate or enhance the natural remodeling of the vein that may occur, e.g., when the vein is exposed to arterial blood pressure. The entire access port 330 may include bands 350 to provide a self-closing access region or may include one or more self-closing regions separated by unsupported regions and/or may include transition regions on the ends of the access port 330, if desired.

In yet another option, any of the access devices described herein may be included in a system or kit including one or more instruments for accessing a tissue structure or graft through the access device. For example, the instrument may include a needle (not shown) including a tip larger than openings through the bands 350 of the access port 330. The tip of the needle may be configured to facilitate passing the needle between the bands 350, e.g., to separate the struts 352, connectors, 354, and/or other features. For example, the needle may include at least one of a coating, a surface treatment, and the like to facilitate passing the needle between the support elements. In addition, the tip may be beveled or tapered, i.e., including a beveled shape, to facilitate inserting the needle through the openings in the bands 350. Optionally, the bands 350 may be configured to facilitate inserting the needle therethrough, e.g., by including tapered or rounded edges on the struts 352, connectors 354, and/or other features.

In addition or alternatively, the needle may include one or more features for limiting the depth of penetration of the tip through the access port 330. For example, the needle may include a bumper (not shown) spaced apart a predetermined distance from the tip to prevent over-penetration of the needle through the access port 330. In an exemplary embodiment, the bumper may be an annular ridge or other feature (not shown) attached around or formed around the needle at a predetermined distance from the tip.

Turning to FIGS. 15-17C, yet another embodiment of an access port 430 is shown that is integrally formed on a tubular structure, such as a tubular graft 410, e.g., formed from ePTFE or other material. Generally, the access port 430 includes a port body 432, a plurality of bands 450, and a fabric covering 460, similar to the previous embodiments. The port body 432 and bands 450 may be formed similar to the methods described above, e.g., such that the bands 450 surround or are embedded in the material of the port body 432, and compress the material laterally and/or radially inwardly to close an opening created through the port body 432. The port body 432 may be formed as a tubular body, e.g., before or after attaching the bands 450, and then the port body 432 may be split, e.g., as described above. The side edges (not shown) of the port body 432 may be separated and the access port 430 positioned around the tubular graft 410. Alternatively, the port body 432 may not be split, and the access port 430 may simply be directed over one end of the graft 410 to a desired location in an enclosed tubular configuration (not shown).

Optionally, in any of the embodiments herein, the port body may be formed from bioabsorbable material, e.g., PLA, PGA, SIS, and the like. In this alternative, once the access port is implanted within a patient's body, e.g., around or otherwise to an existing tissue structure, the bioabsorbable material may be absorbed over time and/or replaced with connective tissue. Thus, the non-bioabsorbable components of the access port, e.g., the bands or other resilient support elements, may remain indefinitely within the patient's body to bias the tissue structure to self-seal after one or more instruments are inserted through the bands or support elements. Thus, the bands or support elements may provide or enhance an elasticity of the tissue structure to accommodate access therethrough.

In a further alternative, the bands or support elements (such as any of those described herein) may be implanted without being embedded within a base material. For example, the bands or support elements may be applied around a tubular structure or to a surface of an organ or other tissue structure (not shown). Optionally, the bands or support elements may be coated or otherwise provided with agents that enhance tissue ingrowth. Thus, over time, tissue may grow into and/or around the struts or other elements of the bands or support elements, thereby integrating the bands or support elements into the tissue. Once so integrated, the bands or support elements may provide self-sealing access sites, similar to other embodiments herein.

Turning to FIGS. 24A-24C, another embodiment of an access port 630 is shown that includes a plurality of annular bands 632 that are at least partially overlapping one another, e.g., such that bands 632 define frustoconical shapes. Each band 632 may be formed from one or more sheets of flexible base material including a plurality of elastic bands or other support elements therein (not shown), similar to other embodiments herein. Alternatively, each band 632 may include a solid panel embedded within flexible base material (also not shown). The support elements may be formed from materials similar to other elements herein, e.g., Nitinol or other superelastic metal, stainless steel, cobalt chromium, or other metal.

As best seen in FIGS. 24B and 24C, each band 632 includes a plurality of panels or sheets 644 attached together, e.g., to define an enclosed tubular shape, or an open configuration that may be wrapped around a tubular structure 610, such as a graft and the like. For example the sheets 644 may be partially overlapped around a periphery of each bands 632 and attached together, e.g., by bonding with adhesive, suturing, and the like. Alternatively, the sheets 644 may be provided separately and attached to the tubular structure 610 one or more at a time, e.g., by attaching a first sheet 644 and then attaching successive sheets 644 that partially overlap one or more sheets 644 already attached to the tubular structure 610.

Turning to FIGS. 25A and 25B, in an alternative embodiment, an access port or device 730 may be provided that includes a plurality of overlapping panels 750 embedded within flexible base or substrate material 732, which may be constructed from materials similar to any of the other embodiments herein. As shown, the panels 750 may include edges 752 that overlap adjacent panels, e.g., in a longitudinal direction (as shown in FIG. 25A) and/or circumferential direction (as shown in FIG. 25B) such that the edges 752 may be separated to provide a passage to accommodate an instrument therethrough (not shown), as described further below.

For example, in the example shown in FIG. 25B, an annular band of panels 750 is provided that includes four panels whose side edges 752*a* partially overlap one another. Further, in the example shown in FIG. 25A, four annular bands of panels 750 are provided along the length of the access port 730 whose end edges 752*b* overlap one another in a frustoconical configuration. It will be appreciated that additional or fewer panels 750 (than the four shown) may be provided to define each band and/or that additional or fewer bands may be provided along the length of the access port 740, as desired.

Similar to other embodiments herein, the access port 730 may be provided as a separate tubular body such that the access port 730 may be attached to a tubular body 710, e.g., a tubular graft or a tubular structure in situ, such as a blood vessel, fistula, or implanted graft. Alternatively, the access port 730 may be provided as a cuff or patch (not shown), e.g., including side edges extending between ends of the access port 730. For example, the access port 730 may have a "C" shaped cross-section or may have a substantially flat or curved shape, if desired, similar to other embodiment herein. The panels 750 may be provided around the entire periphery of the cuff or patch or only partially between the side edges and/or partially along the length of the cuff or patch, as desired. In a further alternative, the panels 750 may be integrally formed into a wall of a tubular structure, such as a tubular graft (not shown).

The panels 750 and/or the base material 732 may be sufficiently flexible such that the panels 750 may be separated partially from one another during use. For example, if an instrument, e.g., a needle and the like (not shown) were penetrated into the access port 730, it may encounter one of the panels 750 and may move along the panel 750 until it encounters the overlapped edges 752 of that panel 750 and an adjacent panel. Inward force of the instrument may cause the overlapped edges 752 to separate partially, e.g., by directing the panel 750 inwardly relative to the adjacent panel. Thus, the instrument may pass freely between the overlapped edges 752 and through the base material 732, e.g., into the underlying tubular body 710. Once the instrument (or other device used with the instrument) is removed, the panels 750 may resiliently return towards their original overlapped configuration, thereby closing and/or substantially sealing the passage created through the access port 730. In addition, as shown, existing pressure within the tubular body 710 may also press outwardly, thereby biasing the panels 750 to return outwardly to enhance the seal created.

Turning to FIG. 1A, an exemplary embodiment of a graft 10 is shown that includes two access ports 30, which may be any of the embodiments herein. The graft 10 may be formed from synthetic or biological material for vascular grafts, e.g., ePTFE, and the like, and the access ports 30 may be integrally formed or attached to the wall of the graft 10 at one or more desired locations, e.g., to allow repeated access during hemodialysis and/or other procedures. The graft 10 includes first and second ends 12, 14, e.g., for attaching or otherwise integrating the graft 10 with the existing vasculature of a patient. As shown, the first end 12 includes a tapered or beveled shape, e.g., to allow the first end 12 to be inserted into the lumen of an existing vessel and/or otherwise attached thereto, e.g., by suturing. The second end 14 includes a sutureless anastomotic coupler, shown in more detail in FIGS. 7A and 7B. It will be appreciated that one or both ends of the graft 10 may include any of the couplers or features described herein.

For example, turning to FIGS. 7A and 7B, an anastomotic flow coupler 70 may be provided on one or both ends of a graft 10, e.g., to facilitate rapid, optionally sutureless, anastomosis, cause less injury, and/or provide a smoother transition from graft to the in situ vessel 90. The coupler 70 may include a highly elastic structure 72 that forms a flared distal end incorporated within the substrate material of the graft 10. For example, the coupler 70 may include a skeleton or other structure 72, such as a stent-like structure, e.g., including substantially straight struts alternately coupled by curved connectors, and fabricated using similar materials and/or processes as the CEB 50, described elsewhere herein.

The elastic structure 72 may be embedded in the material of the graft 10 or may be attached to an outer or inner surface of the graft 10, e.g., by bonding with adhesive, fusing, sonic welding, and the like. At least a portion of the coupler 70, e.g., the flared rim 74, may be covered with fabric or other material, e.g., to enhance tissue ingrowth, or alternatively, the elastic structure 72 may remain exposed. Optionally, the flared rim 74 may have sufficient length to provide a saddle or other shape that may be attached to the vessel 90. The flared rim 74 may be resiliently compressible, e.g., to engage the vessel wall 90 to enhance remodeling of the vessel 90, if desired, similar to other embodiments herein. In addition or alternatively, the flared rim 74 or the elastic structure 72 may provide a self-closing access region, similar to other embodiments herein.

The coupler 70 may be inserted into the native vessel either surgically or percutaneously. For example, a small incision may be created in the vessel wall 90, e.g., less than the diameter of the flared end of the coupler 70, and the flared end of the coupler 70 may inserted through the incision into the lumen. In an exemplary embodiment, the coupler 70 may be sheathed or otherwise constrained, e.g., within a sheath or catheter, to a diameter smaller than the incision, and inserted through the opening and into the lumen. The coupler 70 may then be released, e.g., by deploying the coupler 70 from the sheath such that the flared end resiliently returns to its flared shape, and the graft 10 may be pulled back until the coupler 70 is opposed firmly against the vessel wall 90. Intravascular pressure may further compress the flared rim of the coupler 70 against the vessel wall 90, e.g., to facilitate achieving hemostasis without requiring sutures or other connectors. Optionally, the coupler 70 may also be attached to the vessel 90, e.g., by suturing, bonding with adhesive, and the like, if desired.

Alternatively, the coupler 70 may be plastically deformable rather than self-expanding. For example, the support structure 72 may be formed from plastically deformable material, e.g., stainless steel or other metal, plastic, or composite materials, that may be provided initially substantially straight. Once the coupler 70 has been inserted into an incision in the vessel wall 90, a balloon or other expandable device (not shown), may be introduced into the coupler 70 and/or vessel 90 and expanded to deform the support structure 72 into a desired shape transitioning from the graft 10 to the vessel 90.

Figure 8:
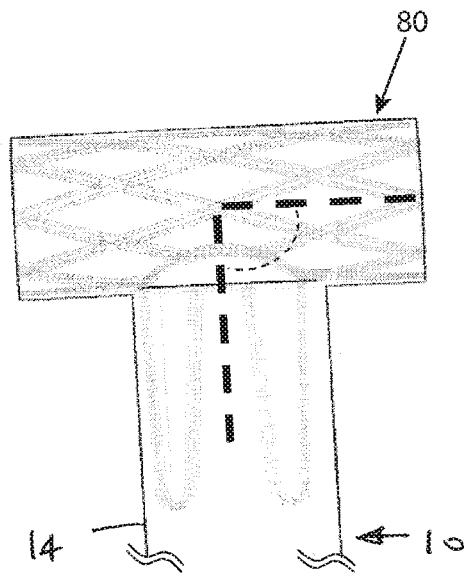
FIG. 8 is a side view of an alternative embodiment of a sutureless anastomosis connector that may be provided on a tubular graft, such as that shown in FIG. 1A.
Figure 9A:
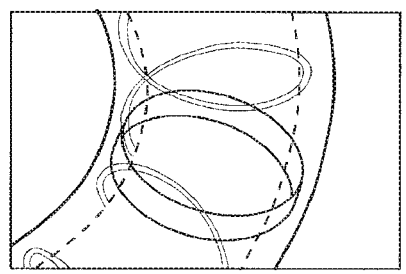
FIG. 9A is a perspective view showing an exemplary embodiment of a flow restrictor device that may be included in a tubular graft, such as that shown in FIG. 1A.
Figure 9C:
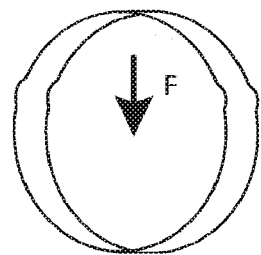
FIGS. 9C and 9D are perspective views of the flow restrictor device of FIGS. 9A and 9B, showing the device in open and restrictive positions, respectively.
Figure 9B:
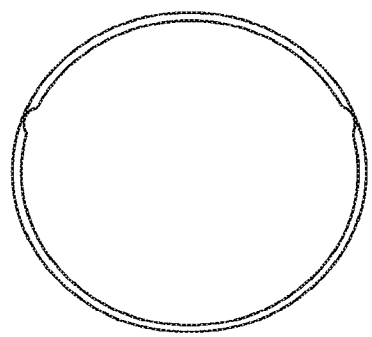
FIG. 9B is an end view of the flow restrictor device of FIG. 9A.
Figure 9D:
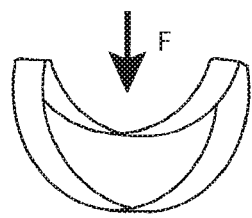

Turning to FIGS. 8A and 8B, an exemplary Flow Conduit (FC) 80 is shown that may be integrated as part of one or both ends of a graft. The FC 80 may provide an anastomotic and/or anti-thrombogenic structure, and is described further in the applications incorporated by reference herein. Although the coupler 70 of FIGS. 7A and 7B and FC 80 of FIGS. 8A and 8B are shown substantially orthogonal to the central axis of the graft, it will be appreciated that the angle of the junction to the vessel 90 may be less than ninety degrees (90°), e.g., between about ten and fifty degrees (10-50°), which may create better flow and/or other transition from the graft to the native vessel.

Figure 21:
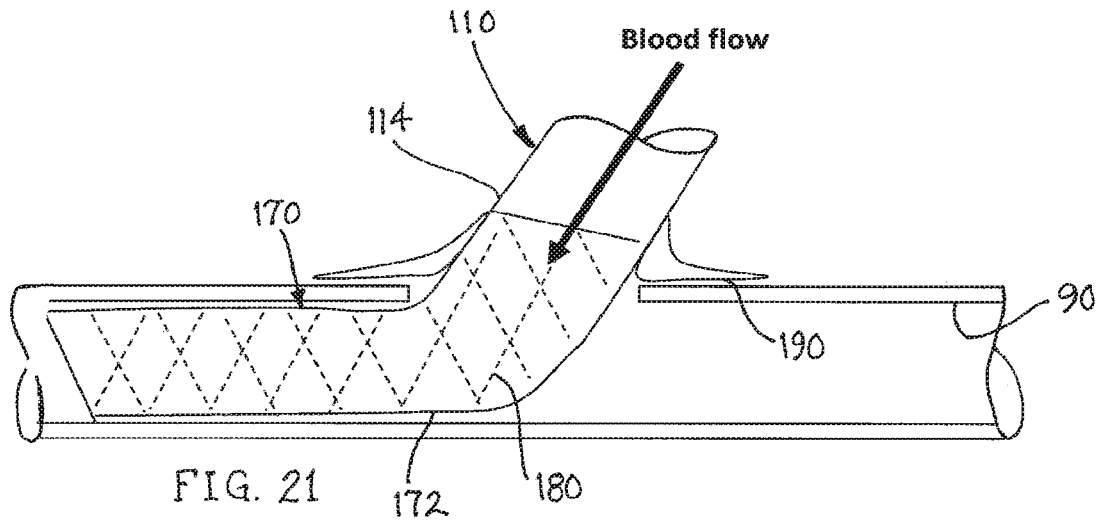
FIG. 21 is a cross-sectional view of a tubular body structure and a side view of one end of a tubular graft being attached to the tubular structure such that a flexible flow coupler on the graft extends into a lumen of the tubular structure.

Turning to FIG. 21, yet another embodiment of a flow coupler 170 is shown that may be provided on one (or each) end 114 of a graft 110 (which may or may not include access port(s) described elsewhere herein, not shown). In this embodiment, the coupler 170 may include a flexible tubular material 172 having an elastic structure 180 embedded or otherwise attached thereto. The tubular material 172 may include fabric or other material that promotes tissue ingrowth, e.g., polyester, ePTFE (with IND between about 50-150 μm), and the like. The elastic structure 180 may include one or more bands or mesh of elastic or superelastic material, e.g., Nitinol, similar to the CEB 50 described above, which may be embedded in the tubular material 172 and/or may be attached to the inner or outer surface of the tubular material 172, e.g., by one or more of suturing, bonding with adhesives, fusing, sonic welding, and the like.

Optionally, as shown, the coupler 170 may include a collar 190, e.g., surrounding the tubular material 172 immediately adjacent to the end 114 of the graft 110 or elsewhere along the length of the coupler 170. The collar 190 may be shaped to be received around a portion of the outer wall of the vessel 90 or within the lumen of the vessel 90. The collar 190 may stabilize or otherwise secure the coupler 170 relative to the vessel 90, and, optionally, may be further secured to the vessel 90, e.g., by suturing, bonding with adhesive, and the like, if desired.

The coupler 170 may have a substantially uniform diameter similar to the graft 110 or may taper or otherwise transition to a different diameter or cross-section, as desired, to provide a desired flow pattern from the graft 110 into the vessel 90, e.g., to reduce thrombosis and/or intimal hyperplasia. The coupler 170 may be sufficiently flexible to accommodate bending without substantial risk of kinking or buckling, e.g., allowing the coupler 170 to bend up to ninety degrees (90°) to transition from the graft 110 to the vessel 90 while providing a substantially smooth interior lumen.

Figure 22:
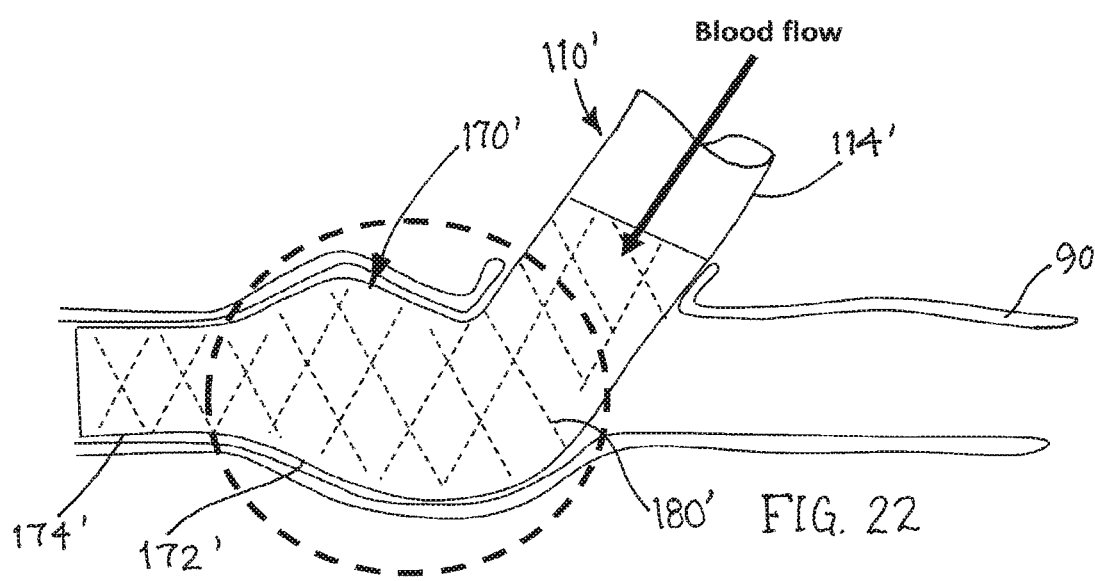
FIG. 22 is a cross-sectional view of a tubular body structure and a side view of one end of another tubular graft being attached to the tubular structure such that a flexible flow coupler on the graft extends into a lumen of the tubular structure.

The elastic structure 180 may simply support the tubular structure 172 or may bias the tubular structure 172 to a desired diameter and/or shape. For example, as shown in FIG. 22, the elastic structure 180' may bias the tubular structure 172' to a bulbous shape, e.g., defining a relatively large diameter region between the end 114' of the graft 110' and the tip 174' of the coupler 170.' Alternatively, the elastic structure 180' may bias the entire coupler 170' to a diameter larger than the diameter of the vessel 90, e.g., to remodel the vessel 90 to a larger diameter or desired shape.

Figure 23:
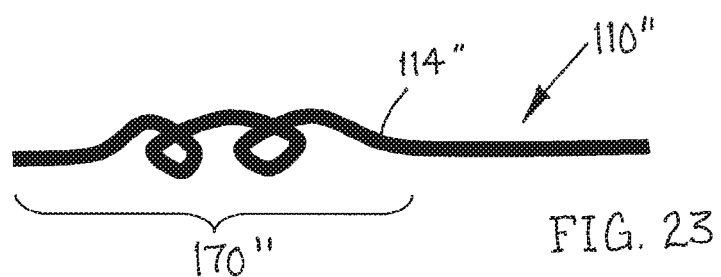
FIG. 23 is a side view of one end of a tubular graft including a flexible flow coupler biased to a spiral shape.

In addition or alternatively, as shown in FIG. 23, a graft 110" may be provided that includes a flow coupler 170" on one end 114" thereof that is biased to a helical or spiral shape. The coupler 170" may be sufficiently flexible to adopt any shape into which it is placed yet may be biased to return towards the helical shape to provide a desired flow characteristic through the coupler 170" after implantation.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the devices described herein may be combined with any of the delivery systems and methods also described herein.

While embodiments of the present invention have been shown and described, various modifications may be made without departing from the scope of the present invention. The invention, therefore, should not be limited, except to the following claims, and their equivalents.

We claim:

1. A method for implanting a vascular access device into a patient's body for performing hemodialysis, comprising:
providing an access device defining a first end, a second end, a longitudinal axis extending therebetween, and a continuous wall formed from elastomeric base material including inner and outer surfaces and defining opposite side edges extending between the first and second ends, the access device comprising a plurality of elongate elastic elements embedded in the base material, and fabric or porous material at least partially covering the base material, the elastic elements separable laterally within the base material to accommodate creating an opening through the base material when an instrument is introduced through the base material during hemodialysis, and biased to return laterally towards a relaxed state for self-closing the opening after removing the instrument;
exposing a tubular body structure within a limb of a patient's body;
wrapping the access device around the body structure such that the inner surface of the access device is positioned against the outer surface of the body structure; and
attaching the access device to the body structure.

2. The method of claim 1, wherein the body structure comprises at least one of a tubular graft, a fistula, and a blood vessel.

3. The method of claim 1, wherein the access device is attached to the body structure using one or more sutures.

4. The method of claim 1, wherein the elastic elements comprise a plurality of bands embedded in the base material, each band comprising longitudinal struts extending substantially parallel to the longitudinal axis and curved connectors connecting alternate ends of the longitudinal struts to define a zigzag pattern such that the zigzag pattern extends between the side edges of the access device.

5. The method of claim 1, wherein the elastic elements comprise a plurality of bands embedded in the base material, each band extending between the first and second ends of the access device.

6. The method of claim 5, wherein the elastic elements comprise a zigzag pattern that zigzags transversely relative to the longitudinal axis while the elastic elements extend generally axially between the first and second ends of the base material.

7. The method of claim 5, wherein the bands extend helically around a periphery of the access device.

8. The method of claim 1, wherein positioning the inner surface of the access device against the outer surface of the body structure, comprises:
separating the side edges of the access device to open the access device;
positioning the access device adjacent the outer surface of the body structure; and
releasing the side edges such that the inner surface of the access device wraps at least partially around the outer surface of the body structure.

9. The method of claim 8, wherein the access device compresses the body structure when the side edges are released.

10. The method of claim 1, wherein the access device is provided in a substantially flat configuration, and wherein positioning the inner surface of the access device against the outer surface of the body structure comprises wrapping the access device at least partially around the body structure.

11. The method of claim 1, wherein the tubular body structure is located within an arm of the patient's body.

12. The method of claim 1, wherein the access device is attached to the body structure by stitching with one or more sutures.

13. A method for implanting a vascular access device into a patient's body for performing hemodialysis, comprising:
exposing a blood vessel within a limb of the patient's body; and
wrapping an access device around the outer surface of the blood vessel, the access device defining a first end, a second end, a longitudinal axis extending therebetween, and a continuous wall having a "C" shaped cross-section formed from elastomeric base material including inner and outer surfaces and defining opposite side edges extending between the first and second ends, the access device comprising a plurality of elastic elements embedded in the base material, and fabric or porous material at least partially covering the base material, the elastic elements separable laterally within the base material to accommodate creating an opening through the base material when an instrument is introduced through the base material during hemodialysis, and biased to return laterally towards a relaxed state for self-closing the opening after removing the instrument; and
attaching the access device to the blood vessel.

14. The method of claim 13, wherein the access device is attached to the blood vessel using one or more sutures.

15. The method of claim 13, wherein the elastic elements comprise a plurality of bands embedded in the base material, each band comprising longitudinal struts extending substantially parallel to the longitudinal axis and curved connectors connecting alternate ends of the longitudinal struts to define a zigzag pattern such that the zigzag pattern extends between the side edges of the access device.

16. The method of claim 13, wherein the elastic elements comprise a plurality of bands embedded in the base material, each band extending between the first and second ends of the access device.

17. The method of claim 16, wherein the elastic elements comprise a zigzag pattern that zigzags transversely relative to the longitudinal axis while the elastic elements extend generally axially between the first and second ends of the base material.

18. The method of claim 16, wherein the bands extend helically around a periphery of the access device.

19. The method of claim 13, wherein attaching the access device to the outer surface of the blood vessel, comprises:
separating the side edges of the access device to open the access device;
positioning the access device adjacent the outer surface of the body structure; and
releasing the side edges such that the inner surface of the access device wraps at least partially around the outer surface of the body structure.

20. The method of claim 13, wherein the access device is provided in a substantially flat configuration, and wherein positioning the inner surface of the access device against the outer surface of the body structure comprises wrapping the access device at least partially around the body structure.

21. A method for implanting a vascular access device into a patient's body for performing hemodialysis, comprising:
exposing one or more blood vessels within the patient's body; and
attaching opposite ends of a tubular graft to ends of the one or more blood vessels, the tubular graft defining a longitudinal axis extending between the opposite ends and comprising an access device on a sidewall thereof extending partially between the opposite ends along the longitudinal axis, the access device defining a first end, a second end, and a continuous wall extending around an outer surface of the tubular graft and between the first and second ends of the access device formed from elastomeric base material including inner and outer surfaces extending between the first and second ends, the access device comprising a plurality of elastic elements embedded in the base material, the elastic elements separable laterally within the base material to accommodate creating an opening through the base material when an instrument is introduced through the base material, and biased to return laterally towards a relaxed state for self-closing the opening after removing the instrument.

22. The method of claim 21, wherein the elastic elements comprise a plurality of bands embedded in the base material, each band extending between the first and second ends of the access device.

23. The method of claim 22, wherein the bands extend helically around a periphery of the access device.

24. The method of claim 22, wherein the graft includes a coupler on a first end of the graft for coupling the first end to one of the one or more blood vessels.

25. The method of claim 21, wherein attaching the tubular graft comprises forming suture based anastomotic junctions to connect ends of the tubular graft to the ends of the one or more blood vessels.

26. The method of claim 21, wherein exposed surfaces of the access device are covered with synthetic fabric or porous material.

27. The method of claim 21, wherein the one or more blood vessels comprise a vein and an artery, and wherein one of the first and second ends is attached to the vein and the other of the first and second ends is attached to the artery.

* * * * *